United States Patent
Shapiro et al.

(10) Patent No.: US 7,396,932 B2
(45) Date of Patent: Jul. 8, 2008

(54) PROCESS FOR PREPARING 4,5-DIHYDRO-PYRAZOLO[3,4-C]PYRID-2-ONES

(75) Inventors: Rafael Shapiro, Wilmington, DE (US); Lucius T Rossano, West Windsor, NJ (US); Boguslaw M Mudryk, East Windsor, NJ (US); Nicolas Cuniere, Belle Mead, NJ (US); Matthew Oberholzer, Wilmington, DE (US); Huiping Zhang, Belle Mead, NJ (US); Bang-Chi Chen, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 379 days.

(21) Appl. No.: 11/235,510

(22) Filed: Sep. 26, 2005

(65) Prior Publication Data
US 2006/0069258 A1  Mar. 30, 2006

Related U.S. Application Data

(60) Provisional application No. 60/688,999, filed on Jun. 9, 2005, provisional application No. 60/613,938, filed on Sep. 28, 2004.

(51) Int. Cl.
| | | |
|---|---|---|
| C07D 471/02 | (2006.01) | |
| C07D 491/02 | (2006.01) | |
| C07D 498/02 | (2006.01) | |
| C07D 513/02 | (2006.01) | |
| C07D 515/02 | (2006.01) | |

(52) U.S. Cl. .................................................... 546/120
(58) Field of Classification Search ................ 546/120
See application file for complete search history.

(56) References Cited

U.S. PATENT DOCUMENTS

| 6,919,451 | B2 | 7/2005 | Zhou et al. |
| 6,967,208 | B2 | 11/2005 | Pinto et al. |
| 2004/0220174 | A1 | 11/2004 | Pinto et al. |
| 2005/0124602 | A1 | 6/2005 | Pinto et al. |
| 2005/0171085 | A1 | 8/2005 | Pinto et al. |
| 2005/0245566 | A1 | 11/2005 | Zhou et al. |
| 2005/0261287 | A1 | 11/2005 | Pinto et al. |
| 2005/0267097 | A1 | 12/2005 | Pinto et al. |

FOREIGN PATENT DOCUMENTS

| WO | WO 03026652 | 4/2003 |
| WO | 03/048081 | * 6/2003 |
| WO | WO03/048158 | 6/2003 |
| WO | WO 03049681 | 6/2003 |
| WO | WO2006/045756 A1 | 5/2006 |
| WO | WO2006/078331 A2 | 7/2006 |

OTHER PUBLICATIONS

U.S. Appl. No. 11/235,647, filed Sep. 26, 2005, Mudryk et al.
U.S. Appl. No. 11/235,327, filed Sep. 26, 2005, Wei et al.
U.S. Appl. No. 11/235,731, filed Sep. 26, 2005, Zhang et al.
U.S. Appl. No. 11/234,942, filed Sep. 26, 2005, Zhao et al.

* cited by examiner

*Primary Examiner*—D. Margaret Seaman
*Assistant Examiner*—Niloofar Rahmani
(74) *Attorney, Agent, or Firm*—Fitzpatrick, Cella, Harper & Scinto

(57) ABSTRACT

A novel process and intermediates thereof for making 4,5-dihydro-pyrazolo[3,4-c]pyrid-2-ones of the type shown below from appropriate phenyl hydrazines is described.

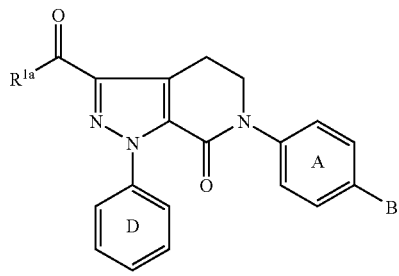

III

These compounds can be useful as factor Xa inhibitors.

39 Claims, No Drawings

PROCESS FOR PREPARING 4,5-DIHYDRO-PYRAZOLO[3,4-C]PYRID-2-ONES

CROSS-REFERENCE TO RELATED APPLICATIONS

This application claims a benefit of priority from U.S. Provisional Application No. 60/613,938 filed Sep. 28, 2004, and U.S. Provisional Application No. 60/688,999 filed Jun. 9, 2005, the entire disclosure of which is herein incorporated by reference.

FIELD OF THE INVENTION

The present invention relates generally to processes for the preparation of 4,5-dihydro-pyrazolo[3,4-c]pyrid-2-ones and intermediates for the synthesis of the same, such pyrazolopyridinones can be useful as factor Xa inhibitors.

BACKGROUND OF THE INVENTION 4,5-Dihydro-pyrazolo[3,4-c]pyrid-2-one compounds, like those described in WO 03/26652, are currently being studied as factor Xa inhibitors in clinical settings. Clinical trials and NDA submissions require practical, large-scale synthesis of the active drug and intermediates for making the active drug. Consequently, it is desirable to find new synthetic procedures for making 4,5-dihydro-pyrazolo[3,4-c]pyrid-2-ones.

SUMMARY OF THE INVENTION

Accordingly, the present invention relates to a novel process for making 4,5-dihydro-pyrazolo[3,4-c]pyrid-2-ones.

The present invention relates to novel intermediates for the syntheses of 4,5-dihydro-pyrazolo[3,4-c]pyrid-2-ones.

These and other objects, which will become apparent during the following detailed description of processes relating to compounds of formula III.

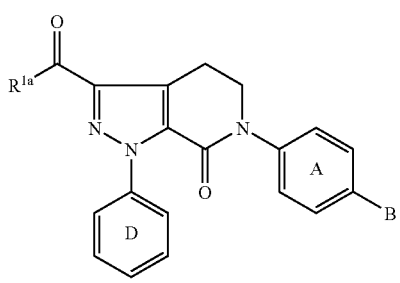

III

DETAILED DESCRIPTION OF THE INVENTION

Thus, in a 1$^{st}$ embodiment, the present invention provides a novel process for preparing a compound of formula III, comprising:

(a) contacting a compound of formula I with a compound of formula II in the presence of a first base;

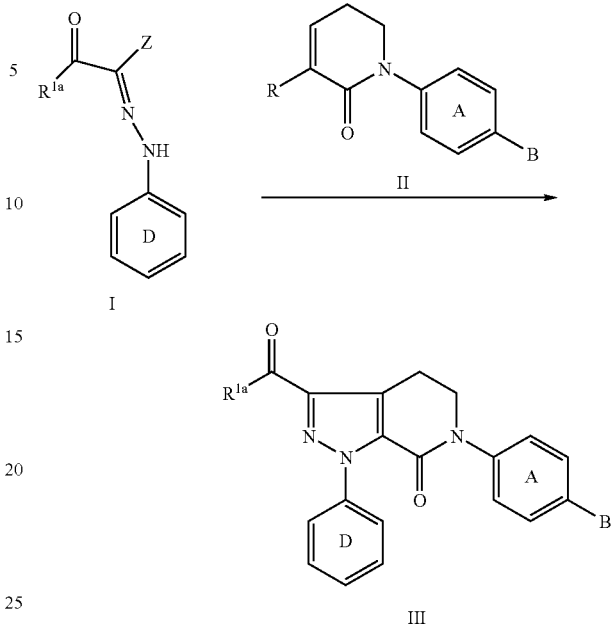

wherein:

Z is selected from Cl, Br, I, $OSO_2Me$, $OSO_2Ph$, and $OSO_2Ph\text{-p-Me}$;

ring D is selected from phenyl, 2-fluorophenyl, 3-chlorophenyl, and 4-methoxyphenyl;

$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;

R is selected from Cl, Br, I, $C_{1-6}$ alkoxy, and $NR^1R^2$;

$R^1$ and $R^2$ are independently selected from $C_{1-6}$ alkyl, cyclopropyl, cyclobutyl, cyclopentyl, cyclohexyl, phenyl, and benzyl;

alternatively, $NR^1R^2$ is a 3-8 membered ring consisting of: carbon atoms, N, and 0-1 O atoms;

ring A is substituted with 0-1 $R^4$;

B is $NO_2$; and $R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 2$^{nd}$ embodiment, the present invention provides a novel process wherein:

Z is selected from Cl, Br, and I;

ring D is selected from 3-chlorophenyl and 4-methoxyphenyl;

$R^{1a}$ is selected from $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;

R is selected from Cl, Br, I, and $NR^1R^2$;

$NR^1R^2$ is selected from morpholino, pyrrolidino, and piperidino;

ring A is substituted with 0-1 $R^4$; and $R^4$ is selected from H and F.

In a 3rd embodiment, the present invention provides a novel process wherein:
Z is Cl;
ring D is 4-methoxyphenyl;
$R^{1a}$ is $OCH_2CH_3$;
R is morpholino; and
ring A is unsubstituted.

In a 4th embodiment, in reaction (a), the compound of formula I is contacted with the compound of formula II followed by the addition of the first base.

In a 5th embodiment, the first base in reaction (a) is a substituted amine base.

In a 6th embodiment, the substituted amine base is selected from: triethylamine, diisopropylethylamine, dabco, DBN, DBU, and N-methylmorpholine.

In a 7th embodiment, the substituted amine base is triethylamine.

In a 8th embodiment, in reaction (a), the contacting is performed in the presence of a first aprotic solvent.

In an 9th embodiment, the first aprotic solvent is toluene.

In a 10th embodiment, reaction (a) further comprises contacting with a first strong acid.

In an 11th embodiment, the first acid is HCl.

In a 12th embodiment, the present invention provides a novel process for preparing a compound of formula IV:

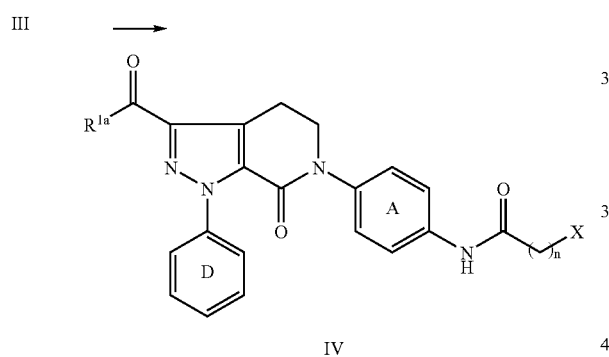

IV the process, comprising:
(b) reducing the B group of formula III to an amino group; and
(c) contacting the resulting amino compound with an alkyl-acid halide to form a compound of formula IV;
wherein:
alkyl-acid halide is $X—C_{3-5}$-alkylene-$C(O)—X_1$;
X is selected from the group Cl, Br, and I;
$X_1$ is selected from the group Cl, Br, $OS(O)_2CH_3$, $OS(O)_2CF_3$, $OS(O)_2$-phenyl, and $OS(O)_2$-tolulyl;
n is selected from the group 3, 4, and 5;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
ring A is substituted with 0-1 $R^4$;
B is $NO_2$; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 13th embodiment, the present invention provides a novel process wherein:
alkyl-acid halide is $X—(CH_2)_4—C(O)—X_1$;
X is selected from the group Cl and Br;
$X_1$ is Cl;
n is 4;
ring D is selected from 3-chlorophenyl and 4-methoxyphenyl;
$R^{1a}$ is selected from $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;
ring A is substituted with 0-1 $R^4$; and $R^4$ is selected from H and F.

In a 14th embodiment, the present invention provides a novel process wherein:
X is Cl;
$X_1$ is Cl;
n is 4;
ring D is 4-methoxyphenyl;
$R^{1a}$ is $OCH_2CH_3$; and
ring A is unsubstituted.

In a 15th embodiment, reaction (b) is performed in the presence of hydrogen, a first catalyst, and a second aprotic solvent.

In a 16th embodiment, in reaction (b), the first catalyst is selected from Pd/C and $Pd/Al_2O_3$ and the second aprotic solvent is selected from N-methylpyrrolidinone, DMSO, DMF, DMAC, and THF.

In a 17th embodiment, in reaction (b), the first catalyst is $Pd/Al_2O_3$ and the second aprotic solvent is N-methylpyrrolidinone.

In an 18th embodiment, the reduction solution resulting from reaction (b) is filtered prior to contacting with the alkyl-acid halide in reaction (c).

In a 19th embodiment, the present invention provides a novel process for preparing a compound of formula V:

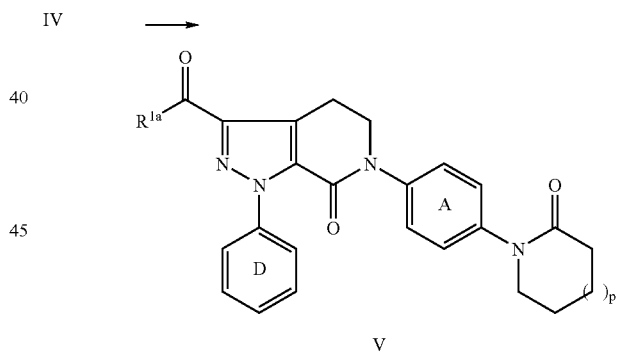

V the process, comprising:
(d) cyclizing the compound of formula IV to form a compound of formula V; wherein:
p is selected from the group 0, 1, and 2;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
ring A is substituted with 0-1 $R^4$; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH$ qj$(CH_3)_2$, $CH(CH_3)CH_2CH_3$, $CH(CH_3)_3$, —CN, and $CF_3$.

In a 20th embodiment, the present invention provides a novel process wherein:

p is 1;

ring D is selected from 3-chlorophenyl and 4-methoxyphenyl;

$R^{1a}$ is selected from $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;

ring A is substituted with 0-1 $R^4$; and $R^4$ is selected from H and F.

In a 21st embodiment, the present invention provides a novel process wherein:

p is 1;

ring D is 4-methoxyphenyl;

$R^{1a}$ is $OCH_2CH_3$; and ring A is unsubstituted.

In a 22nd embodiment, reaction (d) is performed in the presence of first chemical dehydrating agents.

In a 23rd embodiment, in reaction (d), the first dehydrating agents are a second strong acid and a first orthoformate.

In a 24th embodiment, in reaction (d), the second strong acid is TFA and the first orthoformate is triethyl orthoformate.

In a 25th embodiment, in reaction (d), a sodium alkoxide is added after compound IV has been contacted with the first chemical dehydrating agents.

In a 26th embodiment, in reaction (d), the sodium alkoxide is sodium ethoxide.

In a 27th embodiment, cyclizing reaction (d) is performed in the present of a third aprotic solvent.

In a 28th embodiment, the third aprotic solvent is N-methylpyrrolidinone.

In a 29th embodiment, the contacting solution resulting from reaction (c) is used directly in reaction (d).

In a 30th embodiment, the reduction solution resulting from reaction (b) is filtered prior to contacting with the alkyl-acid halide in reaction (c) and the contacting solution resulting from reaction (c) is used directly in reaction (d).

In a 31st embodiment, the present invention provides a novel process for preparing a compound of formula VI:

V →

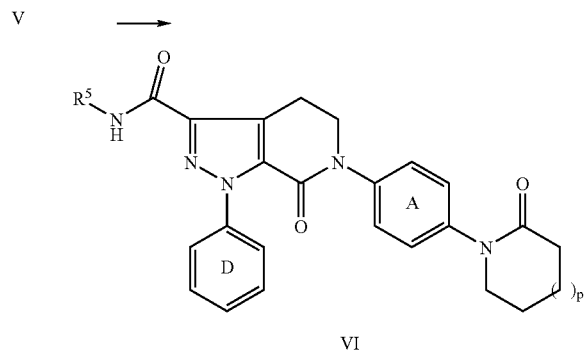

VI the process, comprising:

(e) amidating ester $R^{1a}$ of the compound of formula V to form a compound of formula VI;

wherein:

p is selected from the group 0, 1, and 2;

ring D is selected from phenyl, 2-fluorophenyl, 3-chlorophenyl, and 4-methoxyphenyl;

$R^{1a}$ is selected from $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;

ring A is substituted with 0-1 $R^4$;

$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$; and $R^5$ is selected from H, $CH_3$, and $CH_2CH_3$.

In a 32nd embodiment, the present invention provides a novel process wherein:

p is 1;

ring D is selected from 3-chlorophenyl and 4-methoxyphenyl;

$R^{1a}$ is $CO_2CH_2CH_3$;

ring A is substituted with 0-1 $R^4$;

$R^4$ is selected from H and F; and $R^5$ is H.

In a 33rd embodiment, the present invention provides a novel process wherein:

p is 1;

ring D is 4-methoxyphenyl;

$R^{1a}$ is $CO_2CH_2CH_3$; and ring A is unsubstituted.

In a 34th embodiment, reaction (e) is performed by contacting the compound of formula V with a formamide in the presence of a second base and a fourth aprotic solvent, wherein:

the formamide is $HC(O)NHR^5$;

the second base is an alkoxide; and $R^5$ is selected from H, $CH_3$, and $CH_2CH_3$.

In a 35th embodiment, in reaction (e), the formamide is $HC(O)NH_2$;

the second base is a $C_{1-6}$ alkoxide and the counterion is selected from Li, Na, K, Li, and Mg; and the fourth aprotic solvent is DMF.

In a 36th embodiment, in reaction (e), the second base is a sodium $C_{1-2}$ alkoxide.

In a 37th embodiment, in reaction (e), the second base is NaOMe.

In a 38th embodiment, in reaction (e) the compound of formula V and the fourth aprotic solvent are contacted with second chemical dehydrating agents prior to contacting with the second base.

In a 39th embodiment, in reaction (e), the second dehydrating agents are a third strong acid and a second orthoformate.

In a 40th embodiment, in reaction (e), the third strong acid is TFA and the orthoformate is trimethyl orthoformate.

In a 41st embodiment, the present invention provides a novel compound of formula IIa:

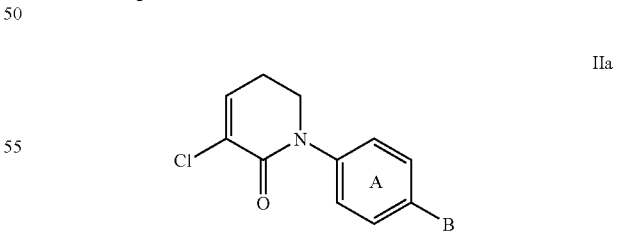

IIa wherein:

ring A is substituted with 0-1 $R^4$;

B is $NO_2$; and $R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 42$^{nd}$ embodiment, the present invention provides a novel compound of formula III:

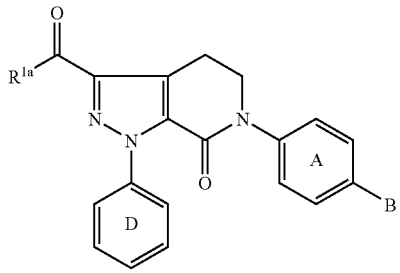

III wherein:
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
ring A is substituted with 0-1 $R^4$;
B is $NO_2$; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 43$^{rd}$ embodiment, the present invention provides a novel compound of of formula IV:

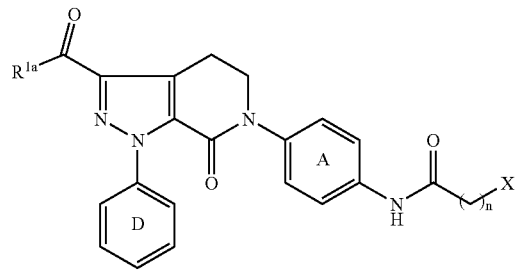

IV wherein:
X is selected from the group Cl, Br, and I;
n is selected from the group 3, 4, and 5;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
ring A is substituted with 0-1 $R^4$;
B is $NO_2$; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 44$^{th}$ embodiment, the present invention provides a novel compound of formula V:

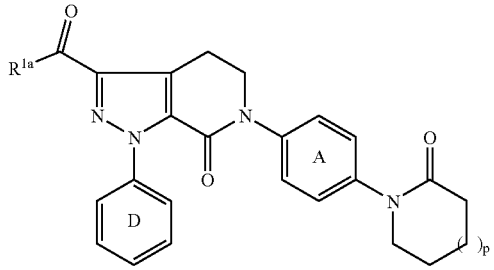

V wherein:
p is selected from the group 0, 1, and 2;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
ring A is substituted with 0-1 $R^4$; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

In a 45$^{th}$ embodiment, the present invention provides a novel process for preparing a compound of formula V:

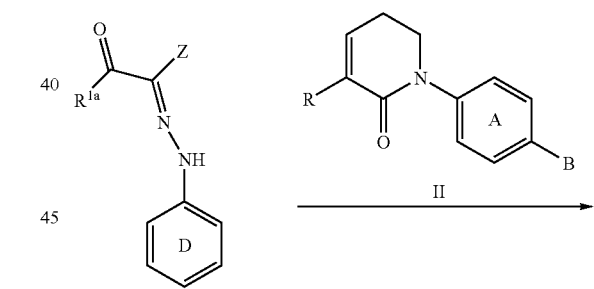

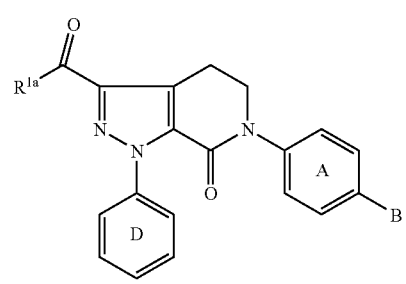

III

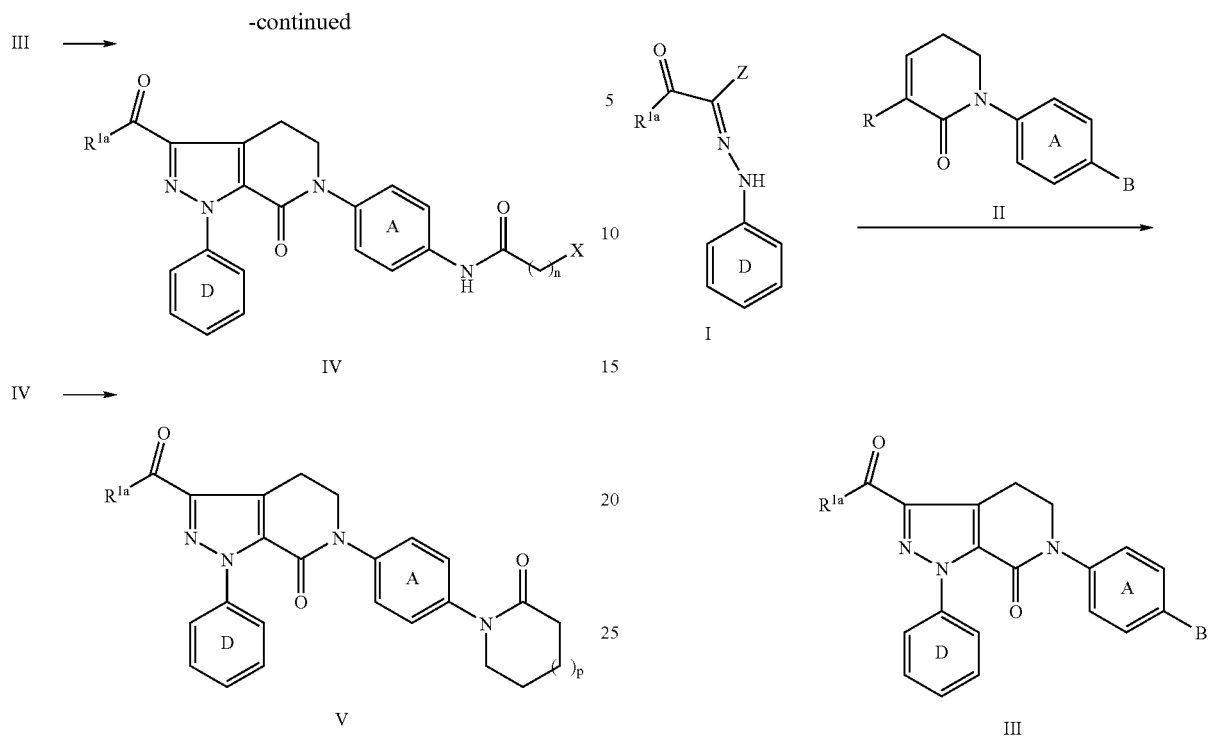

the process, comprising:
  contacting a compound of formula I with a compound of formula II in the presence of a first base;
  reducing the B group of formula III to an amino group;
  contacting the resulting amino compound with an alkyl-acid halide to form a compound of formula IV; and
  cyclizing the compound of formula IV to form a compound of formula V;
  wherein:
  Z is selected from Cl, Br, I, $OSO_2Me$, $OSO_2Ph$, and $OSO_2Ph$-p-Me;
  alkyl-acid halide is X—$C_{3-5}$-alkylene-C(O)—$X_1$;
  X is selected from the group Cl, Br, and I;
  $X_1$ is selected from the group Cl, Br, $OS(O)_2CH_3$, $OS(O)_2CF_3$, $OS(O)_2$-phenyl, and $OS(O)_2$-tolulyl;
  n is selected from the group 3, 4, and 5;
  p is selected from the group 0, 1, and 2;
  ring D is selected from phenyl, 2-fluorophenyl, 3-chlorophenyl, and 4-methoxyphenyl;
  $R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
  R is selected from Cl, Br, I, $C_{1-6}$ alkoxy, and $NR^1R^2$;
  $R^1$ and $R^2$ are independently selected from $C_{1-6}$ alkyl, cyclopropyl, cyclobutyl, cyclopentyl, cyclohexyl, phenyl, and benzyl;
  alternatively, $NR^1R^2$ is a 3-8 membered ring consisting of: carbon atoms, N, and 0-1 O atoms;
  ring A is substituted with 0-1 $R^4$;
  B is $NO_2$; and
  $R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.
  In a 46$^{th}$ embodiment, the present invention provides a novel process for preparing a compound of formula VI:

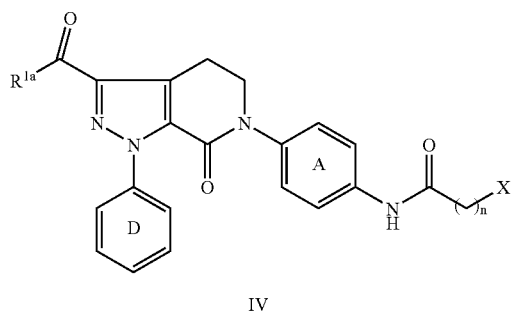

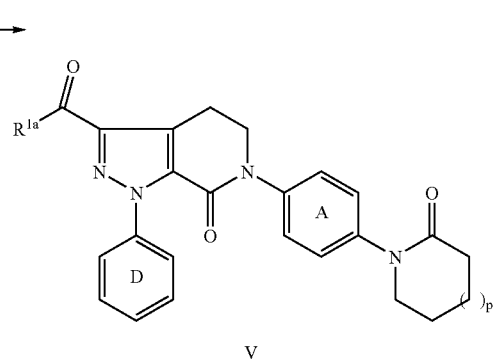

V →

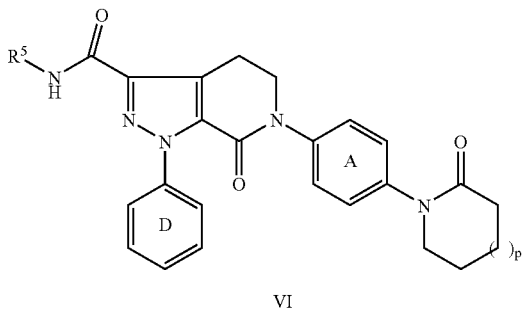

VI the process, comprising:
contacting a compound of formula I with a compound of formula II in the presence of a first base;
reducing the B group of formula III to an amino group;
contacting the resulting amino compound with an alkyl-acid halide to form a compound of formula IV;
cyclizing the compound of formula IV to form a compound of formula V; and
amidating ester $R^{1a}$ of the compound of formula V to form a compound of formula VI;

wherein:
Z is selected from Cl, Br, I, $OSO_2Me$, $OSO_2Ph$, and $OSO_2Ph$-p-Me;
alkyl-acid halide is X—$C_{3-5}$-alkylene-C(O)—$X_1$;
X is selected from the group Cl, Br, and I;
$X_1$ is selected from the group Cl, Br, $OS(O)_2CH_3$, $OS(O)_2CF_3$, $OS(O)_2$-phenyl, and $OS(O)_2$-tolulyl;
n is selected from the group 3, 4, and 5;
p is selected from the group 0, 1, and 2;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
R is selected from Cl, Br, I, $C_{1-6}$ alkoxy, and $NR^1R^2$;
$R^1$ and $R^2$ are independently selected from $C_{1-6}$ alkyl, cyclopropyl, cyclobutyl, cyclopentyl, cyclohexyl, phenyl, and benzyl;
alternatively, $NR^1R^2$ is a 3-8 membered ring consisting of: carbon atoms, N, and 0-1 O atoms;
ring A is substituted with 0-1 $R^4$;
B is $NO_2$;
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$; and
$R^5$ is selected from H, $CH_3$, and $CH_2CH_3$.

The present invention may be embodied in other specific forms without departing from the spirit or essential attributes thereof. Thus, the above embodiments should not be considered limiting. Any and all embodiments of the present invention may be taken in conjunction with any other embodiment or embodiments to describe additional embodiments. Each individual element of the embodiments is its own independent embodiment. Furthermore, any element of an embodiment is meant to be combined with any and all other elements from any embodiment to describe an additional embodiment.

In addition, the present invention encompasses combinations of different embodiment, parts of embodiments, definitions, descriptions, and examples of the invention noted herein.

Definitions
All examples provided in the definitions as well as in other portions of this application are not intended to be limiting, unless stated.

The present invention can be practiced on multigram scale, kilogram scale, multikilogram scale, or industrial scale. Multigram scale, as used herein, is can be in the scale wherein at least one starting material is present in 10 grams or more, at least 50 grams or more, or at least 100 grams or more. Multikilogram scale means the scale wherein more than one kilo of at least one starting material is used. Industrial scale means a scale which is other than a laboratory sale and which is sufficient to supply product sufficient for either clinical tests or distribution to consumers.

Equivalents mean molar equivalents unless otherwise specified.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

"Substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention includes all stable oxides of thiol and amino groups, even when not specifically written. When an amino group is listed as a substituent, the N-oxide derivative of the amino group is also included as a substituent. When a thiol group is present, the S-oxide and S,S-dioxide derivatives are also included.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

"Alkylene" includes both branched and straight-chain saturated aliphatic hydrocarbon groups having the specified number of carbon atoms. $C_{3-5}$ alkylene, includes $C_3$, $C_4$, and $C_5$ alkylene groups. Examples of alkylene include n-propylene, i-propylene, n-butylene, and s-butylene.

The reactions of the synthetic methods claimed herein may be carried out in the presence of a suitable base, said suitable base being any of a variety of bases, the presence of which in the reaction facilitates the synthesis of the desired product. Suitable bases may be selected by one of skill in the art of organic synthesis. Suitable bases include inorganic bases such as alkyl lithium, hydrides, lithium amides, alkali metal, alkali earth metal, thallium hydroxides, and ammonium hydroxides; alkoxides; phosphates; and, carbonates such as sodium hydroxide, potassium hydroxide, sodium carbonate, potassium carbonate, cesium carbonate, thallium hydroxide, thallium carbonate, tetra-n-butylammonium carbonate, and ammonium hydroxide. Suitable bases include methyl lithium, ethyl lithium, n-propyl lithium, i-propyl lithium, n-butyl lithium, i-butyl lithium, s-butyl lithium, t-butyl lithium, hexyl lithium, lithium bis(trimethylsilyl)amide, lithium diisopropylamide, lithium 2,2,2,-tetramethylpiperidine, potassium bis(trimethylsilyl)amide, potassium hydride, or sodium hydride.

"Substituted amine base" includes a tertiary amine base. Examples include trialkylamines wherein the three alkyl groups can be the same or different. Examples of alkyl include methyl, ethyl, n-propyl, i-propyl, n-butyl, s-butyl, t-butyl, n-pentyl, and s-pentyl. The alkyl groups on the substituted amine base also include cycloakyl groups (e.g., cyclopropyl, cyclobutyl, cyclopentyl, and cyclohexyl) and cycloalkyl-alkyl groups (e.g., cyclopropyl-methyl, cyclobutyl-methyl, cyclopentyl-methyl, and cyclohexyl-methyl). Substituted amine bases can also include monocyclic, bicyclic, and tryicyclic amine bases. Examples of substituted amine bases include triimethylamine, triethylamine, tri-n-propylamine, diisopropylethylamine, dabco (1,4-diazabicyclo[2.2.2]octane), DBN (1,5-diazabicyclo[4.3.0]non-5-ene), and DBU (1,8-diazabicyclo[5.5.0]undec-7-ene).

"Strong base" or "strongly basic conditions" includes alkyl lithiums, lithium amides, hydride bases, other organometallic bases, and t-butoxides. Examples of strong bases include lithium tert-butoxide, sodium tert-butoxide, potassium tert-butoxide, methyl lithium, ethyl lithium, n-propyl lithium, i-propyl lithium, n-butyl lithium, i-butyl lithium, s-butyl lithium, t-butyl lithium, hexyl lithium, lithium bis(trimethylsilyl)amide, lithium diisopropylamide, lithium 2,2,2,-tetramethylpiperidine, potassium bis(trimethylsilyl)amide, potassium hydride, and sodium hydride.

"Strong acid" or "strongly acidic conditions" includes TFA (trifluoroacetic acid), sulfuric acid, and sulfonic acids (e.g., benzene sulfonic acid, toluene sulfonic acid, methyl sulfonic acid, and naphthalene sulfonic acid).

Suitable aprotic solvents include ether solvents, tetrahydrofuran (THF), dimethylformamide (DMF), 1,2-dimethoxyethane (DME), diethoxymethane, dimethoxymethane, dimethylacetamide (DMAC), benzene, toluene, 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

"Pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Stable compound" and "stable structure" indicate a compound that is sufficiently robust to survive isolation to a useful degree of purity from a reaction mixture, and formulation into an efficacious therapeutic agent.

"Substituted" indicates that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Synthesis

By way of example and without limitation, the present invention may be further understood by the following schemes and descriptions.

Preparation of Hydrazonyl Compounds I

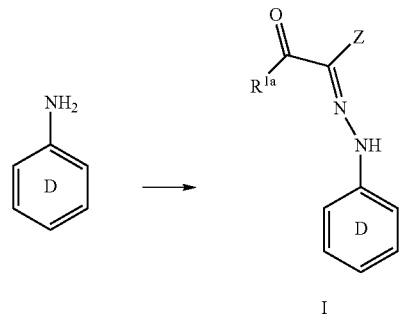

I

The hydrazonyl starting materials of the present invention (formula I) can be made from an appropriate aniline as shown above. A diazenyl group is first made, followed by condensation and elimination to form the hydrazonyl compound. Useful reagents for forming the hydrazinyl group are $NaNO_2$ and HCl. One can first react the aniline with an aqueous acid (e.g., 2-3 equivalents), followed by cooling and addition of aqueous $NaNO_2$ (e.g., about 1-2 equivalents). Other routes to hydrazines known to those of skill in the art could be used. Transformation of the hydrazinyl group to the hydrazonyl group can be achieved by contacting an appropriately substituted acyl compound, wherein the contacting can be in the presence of a base (e.g., NaOAc). For example, when $R^{1a}$ is $CO_2Et$ and Z is Cl, then the starting acyl compound can be $CH_3C(O)CH(Cl)CO_2Et$. Additional $R^{1a}$ groups (e.g., $C_{1-4}$ alkyl, $CF_3$, and other $C_{1-4}$ alkyl esters) and Z groups (e.g., Br, I, $CH_3SO_3-$, phenyl-$SO_3$-, and toluenyl-$SO_3$-) can also be used, depending on the final product. A variety of hydrazonyl groups are described in WO 03/49681, the contents of which are incorporated herein by reference.

Preparation of Dipolarophiles II

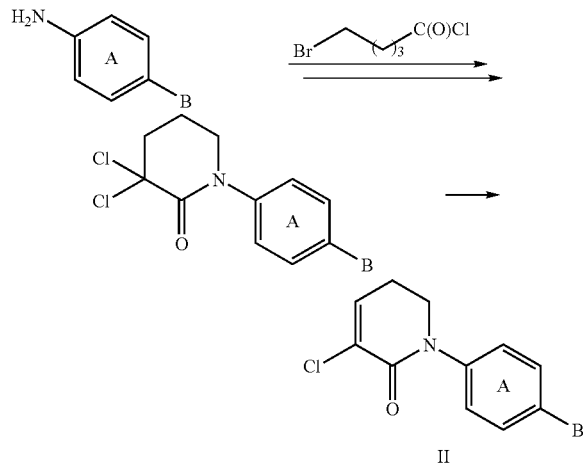

Dipolarophiles II, wherein B is $NO_2$, can be formed from their starting nitro-anilines. One way to achieve lactam formation is by reacting the nitro-aniline with an alkyl-acid chloride such as (a) bromo-valeryl chloride (BVC) or chlorovaleryl chloride (CVC) or (b) BVC. A slight excess of the valeryl chloride can be used. Examples of equivalents of the alkyl-acid chloride include (a) from 1.05, 1.1, 1.15, 1.2, 1.25, 1.3, 1.35, 1.4, 1.45, to 1.5 and (b) 1.15. This initial amide formation can be done in the presence of a base such as $K_2CO_3$ or KOH. Examples of equivalents of base used include (a) from 0.5, 0.6, 0.7, 0.8, 0.9, 1.0, 1.1, 1.2, 1.3, 1.4, to 1.5 and (b) 1.1. An aprotic solvent is generally used (e.g., chlorobenzene and THF). Examples of the amount THF in the solvent based on the weight of chloro-benzene include (a) from 30, 35, 40, 45, 50, 55, 60, 65, 70, 75, 80, 85, 90, 95, to 100% and (a) 50%. Examples of temperatures for the condensation reaction include (a) from 5, 10, 15, 20, 25, 30, to 35° C. and (b) 15° C.

Lactam formation can then be achieved by contacting the resulting amide with a base (e.g., KOH) in the presence of a catalyst (e.g., tetrabutylammonium bromide). Examples of equivalents of base include (a) from 2.0, 2.1, 2.2, 2.3, 2.4, 2.5, 2.6, 2.7, 2.8, 2.9, to 3.0 and (b) 2.0. It is generally useful to maintain a basic pH, for example (a) 11, 12, 13, to 14 and (b) 14. An aprotic solvent is generally used (e.g., chloro-benzene and THF). Examples of the amount THF in the solvent based on the weight of chloro-benzene include (a) from 30, 35, 40, 45, 50, 55, 60, 65, 70, 75, 80, 85, 90, 95, to 100% and (a) 50%.

Examples of temperatures for the condensation reaction include (a) from 5, 10, 15, 20, 25, 30, to 35° C. and (b) 15° C.

Chlorination to the dichloro-intermediate can be achieved by reaction with a chlorinating agent (e.g., $PCl_5$) in an aprotic solvent (e.g., chloro-benzene). Examples of equivalents of chlorinating agent include (a) from 2.5, 2.6, 2.7, 2.8, 2.9, 3.0, 3.1, 3.2, 3.3, 3.4, to 3.5 and (b) 3.0. Examples of temperatures for chlorination include (a) from 25, 30, 35, 40, 45, 50, 55, 60, to 65° C. and (b) about 50° C.

Final conversation to the compound of formula II can be achieved by elimination of one of the chloro groups. One route to the compound of formula II is contacting the dichloro-intermediate with a base (e.g., $Li_2CO_3$) in the presence of a corresponding salt (e.g., LiCl) and an aprotic solvent (e.g., DMF). Examples of equivalents of base include (a) from 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, to 2.0 and (b) about 0.5 equivalents. Examples of equivalents of salt include (a) from 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, to 2.0 and (b) 0.5. Examples of temperatures for the elimination include (a) about 100, 101, 102, 103, 104, 105, 106, 107, 108, 109, 110, 111, 112, 113, 114, 115, 116, 117, 118, 119, 120, 121, 122, 123, 124, to 125° C. and (b) about 105, 106, 107, 108, 109, to 110° C.

Dipolarophiles can also be prepared as shown in U.S. 2003/0181466, the contents of which are incorporated herein.

Reaction (a): 1,3-Dipolar Cycloaddition

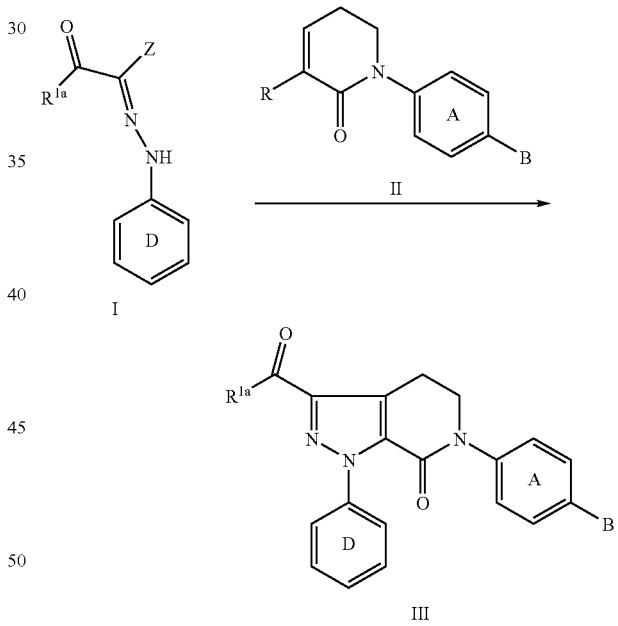

The 1,3-dipolar cycloaddition reaction of the present invention involves reaction between the hydrazonyl compound of formula I and dipolarophile of formula II. This cycloaddition reaction provides the 4,5-dihydro-pyrazolo[3,4-c]pyrid-2-one cores. The reaction can be run in the presence of a substituted amine base (e.g., a non-nucleophilic tertiary amine base). Examples of substituted amine bases include (a) trialkyamines (e.g., triethylamine and diisopropylethylamine) and cyclic tertiary amines (e.g., N-methylmorpholine or DBU), (b) trialkylamines and (c) triethylamine. Examples of equivalents of base used include (a) about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, to 3.5 and (b) 3. Aprotic solvents (e.g., toluene, THF, and DME) can be for the cycloaddition. The cycloaddition can be run from room temperature up to the reflux point of the solvent. Examples of temperatures for the reaction include (a) from about 80, 85, 90, 95, to 100° C. and (b) about 90° C.

Hydrazonyl compound I can first be contacted with the base or dipolarophile (II), followed by addition of the second component. For example, dipolarophile (II) can be contacted with hydrazonyl compound (1) and addition of the base can then follow. Alternatively, the hydrazone (1) can be contacted with a base and addition of dipolarophile (II) can then follow.

Reactions (b) and (c): Amide Formation

III ⟶

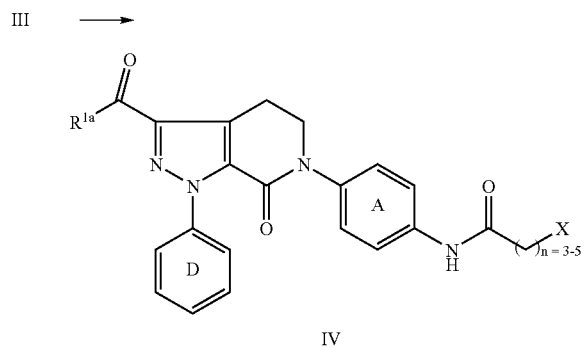

IV

Reduction of group B (e.g., $NO_2$) to its corresponding amine can be achieved using known reducing techniques. Hydrogenation can be performed with a catalyst. Hydrogenation catalysts known to those of skill in the art can be used. Examples of palladium and platinum catalysts include, but are not limited to (a) Pd/C, $Pd/Al_2O_3$, $Pd/CaCO_3$, $Pd/SrCO_3$, Pd/C doped with Fe, Pd/C doped with V, $Pt/Al_2O_3$, $Pt/CaCO_3$, and $Pd/BaCO_3$, (b) $Pd/Al_2O_3$, and (c) 5% $Pd/Al_2O_3$. An aprotic solvent can be used (e.g., N-methylpyrrolidinone, DMSO, DMF, DMAC, and THF). When Pd/C is used as the catalyst, it can be helpful to remove it after hydrogenation by contacting the reduction solution with $Na_2CO_3$. The solution can then be filtered and used in the amidation reaction without further purification, if desired.

Amide IV can be formed by condensation with an appropriate alkyl-acid halide. The halide leaving group of the alkyl-acid halide can be a halide (e.g., Br, Cl, or I) or can be a different type of compatible leaving group (e.g., OMs, OTf, $OS(O)_2$-phenyl, or OTs) to facilitate cyclization to a lactam. Examples of alkyl-acid halides include (a) 4-bromobutyryl chloride, 4-chlorobutyryl chloride, 5-bromovaleryl chloride (BVC), 5-chlorovaleryl chloride (CVC), 6-bromohexanoyl chloride, and 6-chlorohexanoyl chloride, (b) BVC and CVC, and (c) CVC. Examples of equivalents of alkyl-acid halide include (a) from 1.0, 1.01, 1.02, 1.03, 1.04, 1.05, 1.06, 1.07, 1.08, 1.09, 1.1, 1.12, 1.13, 1.14, 1.15, 1.16, 1.17, 1.18, 1.19, 1.2, 1.21, 1.22, 1.23, 1.24, to 1.25 and (b) 1.13. The condensation reaction can be run in the solvent from the reduction reaction. Examples of reaction temperatures include (a) from 15, 20, 25, 30, to 35° C. and (b) 20° C. It may be helpful to add a base to the condensation reaction (e.g., $K_2CO_3$). Examples of equivalents of base include (a) from 0.5, 0.6, 0.7, 0.8, 0.9, 1.0, 1.1, 1.2, 1.3, 1.4, to 1.5 and (b) 1.3. The aprotic solvent used for the reduction can be used in the condensation (e.g., N-methylpyrrolidinone (NMP)). When CVC and NMP are used, the reaction can be run in the absence of a base. The resulting amide can be used in the lactam formation reaction without purification (e.g., the amide/NMP solution can be directly used).

Reaction (d): Lactam Formation

IV ⟶

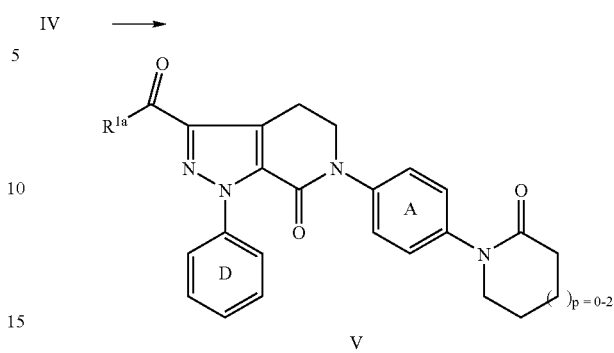

V

The lactam of formula V can be formed by displacing leaving group X in formula IV with its corresponding amide nitrogen. This cyclization can be enhanced by first drying the starting materials with chemical dehydrating reagents. Suitable dehydrating reagents include strong acids and orthoformates. Examples of strong acids include (a) TFA, (b) sulfuric acid, and (c) sulfonic acids. Examples of orthoformates include (a) trimethyl orthoformate, triethyl orthoformate, diethyl phenyl orthoformate, tributyl orthoformate, triisopropyl orthoformate, tripentyl orthoformate, and tripropyl orthoformate and (b) triethyl orthoformate. The amount of orthoformate added depends upon the level of moisture present prior to dehydration and the amount of water desired after dehydration. Examples of the amount of water remaining is less than (a) about 0.1, 0.09, 0.08, 0.07, 0.06, 0.05, 0.04, 0.03, 0.02, to 0.01 wt % of water remaining after dehydration and (b) about 0.03 wt %. For conversion purposes, 0.1 wt % is equivalent to 1000 ppm. Methods known to those of skill in the art (e.g., the Karl Fisher method) can be used to determine water content. After treatment with the acid and formate, the resulting mixture can be contacted with with an alkoxide base to complete the lactamization. Examples of alkoxide bases include (a) sodium methoxide, sodium ethoxide, sodium propoxide, sodium isopropoxide, sodium butoxide, sodium isobutoxide, sodium sec-butoxide, sodium tert-butoxide, potassium methoxide, potassium ethoxide, potassium propoxide, potassium isopropoxide, potassium butoxide, potassium isobutoxide, potassium sec-butoxide, and potassium tert-butoxide and (b) sodium ethoxide. It can be desirable to use an alkoxide base whose alkoxy portion matches that of the formate ester. Examples of equivalents of base used include (a) from 0.5, 0.6, 0.7, 0.8, 0.9, 1.0, 1.1, 1.2, 1.3, 1.4, to 1.5 equivalents of based may be used and (b) 1.3.

Reaction (e): Amidation

V ⟶

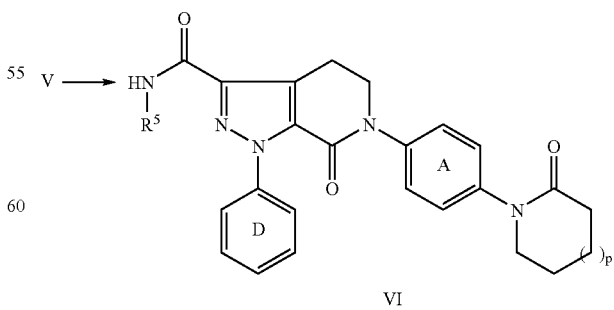

VI

Amide VI can be formed from V (wherein $R^{1a}$ is an ester, e.g., ethyl ester) by contacting with a formamide and a base in the presence of a solvent. Examples of formamide include (a) N-ethyl-formamide, N-methyl-formamide, and formamide itself and (b) formamide itself. Examples of bases include (a) alkoxides, (b) $C_{1-6}$ alkoxide, and (c) methoxide. Examples of counterions for the alkoxide include (a) Li, Na, K, Li, and Mg and (b) Na. Examples of solvents include (a) aprotic solvents and (b) DMF. Examples of reaction temperatures include (a) room temperature up to the reflux point of the solvent used and (b) room temperature to 100° C.

The amidation can be aided by the addition of chemical dehydrating reagents, prior to contacting with the base. Suitable dehydrating reagents include strong acids and orthoformates. Examples of strong acids include (a) TFA, sulfuric acid, and sulfonic acids and (b) TFA. Examples of orthoformates include (a) trimethyl orthoformate, triethyl orthoformate, diethyl phenyl orthoformate, tributyl orthoformate, triisopropyl orthoformate, tripentyl orthoformate, and tripropyl orthoformate and (b) trimethyl orthoformate. The amount of orthoformate added depends upon the level of moisture present prior to dehydration and the amount of water desired after dehydration. Examples of the amount of water remaining is less than (a) about 0.1, 0.09, 0.08, 0.07, 0.06, 0.05, 0.04, 0.03, 0.02, to 0.01 wt % of water remaining after dehydration and (b) about 0.03 wt %. For conversion purposes, 0.1 wt % is equivalent to 1000 ppm.

Other features of the invention will become apparent in the course of the following descriptions of exemplary embodiments which are given for illustration of the invention and are not intended to be limiting thereof.

EXAMPLES

Example 1

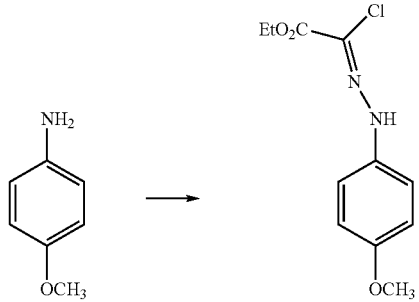

To a 30 gallon glass-lined reactor was charged water (26 L) and p-anisidine (8.5 kg; 68.1 moles). The reactor was inerted, and 20.1 kg 37% HCl (3 eq.) were charged to the reactor followed by a line flush of 2 L purified water. The batch was heated to 40° C. and checked to ensure dissolution of p-anisidine (total time at 40° C. was 25 minutes). The batch was cooled to −2° C. and 40% aqueous sodium nitrite (12.0 kg; 69.5 moles) was charged to the reactor while keeping the temperature at −2±3° C. The addition time for the aqueous sodium nitrite was 35 minutes. The sodium nitrite line was flushed with 2 L of purified water. The reaction mixture was sampled and analyzed for reaction completion. To the batch was added 3.0 kg of 11% aqueous sulfamic acid via nitrogen pressure, keeping the reactor contents at −2±3° C.

In a separate 100 gallon glass-lined reactor, 28 L of purified water was charged followed by 11.2 kg of solid sodium acetate. The reactor was inerted, and the batch was heated to 35° C. until the solid dissolved. The batch was cooled to 15° C. and 18 kg acetone was added to the reactor. To the reactor was added 12.4 kg ethyl-2-chloroacetoacetate by deadhead vacuum, followed by 2.1 kg of acetone to flush the addition line. The batch was cooled to −2±3° C. The contents of the above 30 gallon reactor were then transferred to the 100 gallon reactor keeping the batch in the 100 gallon reactor at −2±3° C. The transfer time was 45 minutes. The transfer line was flushed with 5.0 kg of acetone, and the batch was allowed to mix for one hour. To the reactor was charged 32.0 kg of acetone, and the batch was mixed for 15 minutes. The batch was allowed to settle for 30 minutes. To the reactor was charged 10.2 kg of acetone and the batch was mixed for 5 minutes. Agitation was stopped and the batch was allowed to settle for 30 minutes. The aqueous phase was discharged to a drum (140.2 kg; waste). To the reactor was charged 13.4 kg of methanol, controlling the reactor temperature to 0±3° C. The batch was held at 0±3° C. and sampled every hour until the reaction was complete.

To the reactor was charged 75 L of purified water. The batch was heated to 5±5° C. and allowed to mix for 15 minutes. The batch was isolated using a portable centrifuge with a 5-7 micron polypropylene bag. The isolation lasted 10 minutes (109 kg of centrate). To the reactor was charged 26 L of purified water and 20.2 kg of methanol. The mixture was cooled to 5±3° C. and then discharged to the centrifuge to wash the cake. The wet cake (14.5 kg) was transferred to drying trays covered with FEP liners. The cake was dried at 40° C. for 80 hours to give 13.8 kg of the desired product.

Example 2

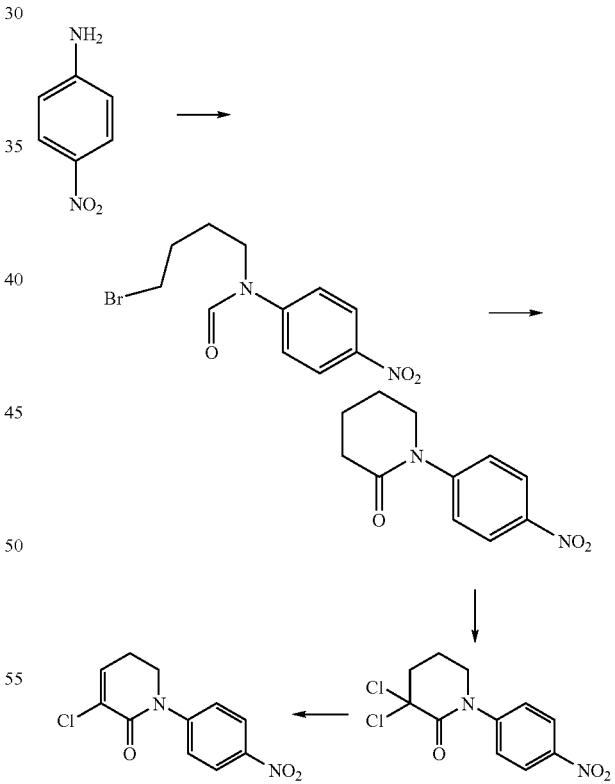

To a 30 gal glass-lined reactor was charged 6.1 kg of 4-nitroaniline. Chlorobenzene (17.5 kg) was charged followed by THF (11.5 kg). Agitation was started at 150 RPM and 13.3 kg of 40% aqueous potassium carbonate was charged to the reactor. The batch was cooled to between 10° C. and 13° C. From a Teflon®-lined pressure cylinder, 9.0 kg of BVC was charged to the reactor while maintaining the reactor temperature between 10° C. and 15° C. The total addition time of the BVC was 37 minutes, and the agitation was increased to 220 RPM. The reaction mass was sampled for reaction completion.

In a separate container, 250 g of tetrabutylammonium bromide (TBAB) was mixed with 500 mL purified water until a clear solution was obtained. This solution was charged to the reactor followed by 12.0 kg of 45% aqueous KOH while maintaining the reactor temperature between 10 and 15° C. (addition time: 12 min). The batch was allowed to mix at 220 RPM for four hours with the reactor jacket set point at 15° C. The batch was sampled for reaction completion. The jacket set point was raised to 20° C., and 0.5 kg aqueous KOH was charged to the reactor. After 45 minutes of mixing, the reaction mass was sampled again. The batch was allowed to mix for 90 minutes and the reaction mass was sampled again.

To the reactor was added 2.0 kg of 37% HCl, and the batch was warmed to 25° C. while mixing for 15 minutes. The batch was sampled for pH (actual: 10 to 11 by paper strips). The entire batch was drummed, and the reactor was rinsed with purified water. The batch was charged back to the reactor through a 5 micron polypropylene filter followed by a 5 kg rinse of chlorobenzene. The batch was allowed to settle for 20 minutes, and the bottom layer was removed. To the reactor was added a sodium chloride solution (2.2 kg NaCl in 9 L purified water) followed by 1 L purified water rinse. The batch was mixed for twenty minutes and allowed to settle overnight. A large cloudy brown rag layer had formed, but it did not separate during the overnight hold. Approximately half of the expected lower phase was removed, and the rag layer was left with the product in the reactor. The batch was distilled under vacuum to remove THF and water to a volume of approximately 22 L; afterward chlorobenzene was charged back. A clear solution was not obtained, so several additional steps were added based on laboratory work. First, 9 L of purified water was charged to the reactor and the batch was mixed for 15 min. The bottom layer (chlorobenzene layer now rich with product) was discharged to a new PE-lined drum, and the top water layer was discharged to a separate drum. The reactor was rinsed with purified water, and the water was discharged from the reactor. The product layer was charged back to the reactor through a 5 micron cotton cartridge filter. The cotton filter appeared to remove much of dark brown insoluble matter. The drum and the transfer line were rinsed with 2 kg of chlorobenzene. The batch was distilled under vacuum to 42 L, and the batch was sampled for THF and H$_2$O content. To the batch was added 10 kg chlorobenzene, and the vacuum distillation was repeated. The batch was sampled again and then cooled to 25° C.

In a dry, water-free 50 gal glass-lined reactor, 27.0 kg PCl$_5$ was charged followed by 43 kg of chlorobenzene. The slurry was heated to 40° C. with 150 RPM agitation. The above-formed chlorobenzene solution was transferred from the 30 gal reactor to the 100 gal reactor over 7 minutes; the reaction temperature did not exceed 50° C. during the addition. The reactor and transfer line were rinsed forward with 5 kg of chlorobenzene. The reaction mass was heated to 55° C. (15 min) and mixed for one hour. The batch was cooled to 25° C. and sampled for reaction completion.

30 L of purified water was used to rinse the 100 gal glass-lined reactor that was used as a distillate receiver during the vacuum distillation of the lactam reaction mass. Care was taken to ensure water was added to the 100 gal reactor, not the 50 gal, which contained the reaction mixture. Following this rinse, 106 L of purified water was added to the 100 gal reactor, and the water was cooled to 5° C. The reaction mass in the 50 gal reactor was transferred to the cold water quench in the 100 gal reactor so that the quenched mass did not exceed a temperature of 25° C. The transfer time was 40 min. After the transfer was complete, 16 kg n-heptane was charged to the 50 gal reactor to rinse the reactor and the transfer line. This rinse was transferred to the 100 gal reactor, and the contents of the 100 gal reactor were allowed to mix overnight at 66 RPM at ambient temperature.

After the overnight hold, 15.4 kg n-heptane was charged to the reactor, and the batch was allowed to mix for 1 hour. A sample was taken and filtered immediately to verify the presence of solid. The batch was filtered on a 36" glass-lined Nutsche filter using a polypropylene bag. The filtration time was 20 minutes. To the 100 gal reactor was charged 21 L of purified water. The water was mixed for 10 minutes to cool and then was discharged to the Nutsche filter to wash the cake. Next, 16.1 kg n-heptane was charged to the 100 gal reactor, mixed for 10 minutes, and then discharged to the Nutsche filter to wash the cake. The wet cake (10.5 kg) was transferred to drying trays covered with FEP liners. The cake was dried at 50° C. for 28 hours to give 8.5 kg of the desired dichloro product.

The dichloro-lactam (16.0 kg) was charged to a 50 gallon glass lined reactor, followed by 1.2 kg of lithium chloride and 2.2 kg of lithium carbonate. The reactor was inerted with nitrogen. To the reactor was charged 31.1 kg DMF and the reactor was heated with mixing to 105 to 110° C. The reaction mixture was held between 105 and 110° C. for four hours and then cooled to 45 to 50° C. for sampling. The reaction mixture was sampled for reaction completion. The batch was then heated to 105 to 110° C. and held for 50 minutes. The batch was cooled to 45 to 50° C. for sampling and sampled for completion. The batch was then heated to 80 to 85° C. Purified water (93 L) was charged from a drum to the reactor using deadhead vacuum maintaining the temperature above 70° C. The batch was cooled to 15 to 20° C. over 35 minutes. The batch was filtered on a portable centrifuge using a 5-7 micron polypropylene bag. The isolation lasted 30 minutes (121 kg centrate collected). To the reactor was added 60 L of purified water. The water was discharged from the reactor to the centrifuge to wash the cake (25 minutes for 60 kg of centrate). To the reactor was added 40.0 kg of isopropyl alcohol. The solvent was discharged from the reactor to the centrifuge to wash the cake (30 minutes for 43.5 kg of centrate). The wet cake (12.8 kg, not including 0.6 kg sample) was transferred to drying trays covered with FEP liners. The cake was dried at 70° C. and full vacuum for nine hours to give 12.8 kg of dried chloro product.

Example 3

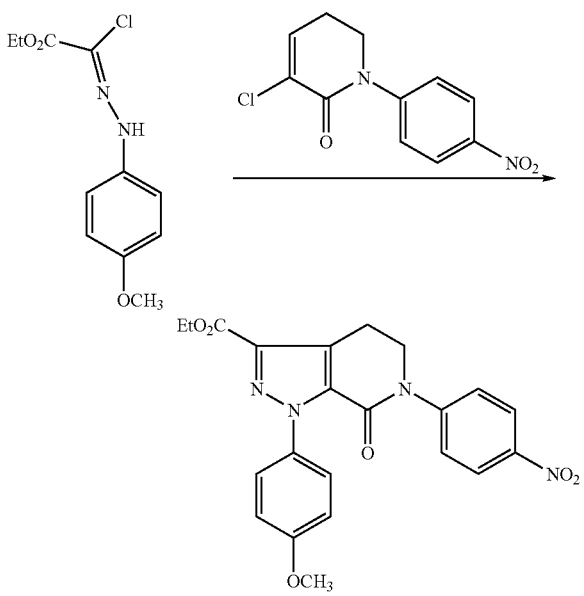

The starting hydrazone (6.5 kg) and tetrahydropyridone (6.0 kg) were charged to a 50 gal glass-lined reactor. To the reactor was added toluene (44.9 kg), and the batch was heated to 90° C. Triethylamine (7.2 kg) was charged to the reactor from a pressure cylinder over 90 minutes, maintaining the batch temperature below 100° C. After the addition, the transfer line was flushed with toluene (1 kg). The reaction mass was mixed at 90° C. for two hours and then cooled to 40° C. for sampling. Purified water (11 L) was added keeping the temperature above 35° C. (5 min). The reaction mixture was cooled to 20° C. over two hours and stirred at 20° C. overnight. The reaction mixture was centrifuged (20 min). To the reactor was charged 42 L of purified water and this water was discharged to the centrifuge. Two distinct liquid layers were observed in the centrate, indicating that the cake had not been fully deliquored. Isopropanol (9.5 kg) was charged to the reactor and then to the centrifuge. This centrate contained two layers as well. The wet cake (10.6 kg) was transferred to drying trays covered with FEP liners. The cake was dried at 50° C. for 33.5 hours to give 9.2 kg of dried product.

Example 4

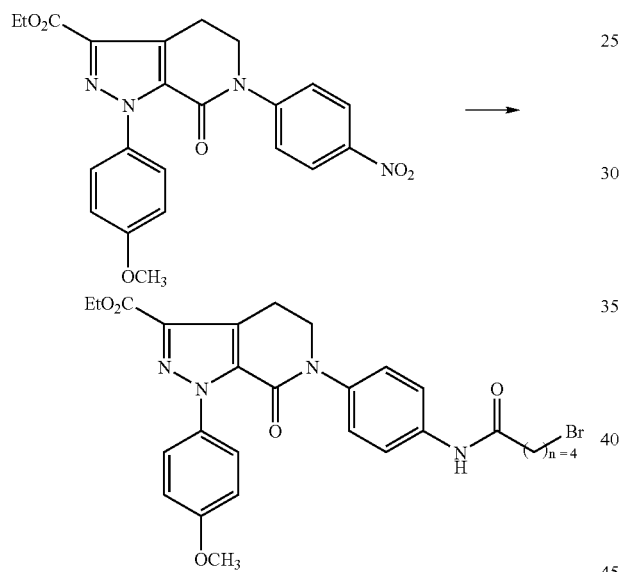

To a 50 gallon Hastelloy reactor was charged 8.0 kg of the starting nitro group and 240 g of Pd/C catalyst (Degussa E101). The reactor was inerted with nitrogen and then 85 kg of tetrahydrofuran was added. The reactor was prepared for hydrogenation following SOP. Agitation was set at 120 RPM and the batch was stabilized at 25° C. Agitation was reduced to 90 RPM and hydrogen was added. The hydrogen set pressure was 3,100 mmHg. The jacket was cooled to 20° C. and agitation increased over 20 minutes until 150 RPM were reached. The jacket temperature was then increased to 40° C. over about 30 minutes. The batch was held at 40° C. for three hours, and then the reactor was depressurized and inerted. Before sampling, the batch was allowed to settle for 10 minutes. The batch was sampled for reaction completion. To the batch was added 120 g Pd/C catalyst slurried in 2.6 kg of THF. The transfer line was rinsed through with 1.4 kg of THF. Agitation was set to 200 RPM, and the reactor was pressurized to 3,100 mmHg hydrogen pressure. The batch was allowed to react for three hours at 40° C. The reactor was depressurized and inerted. The batch was sampled for reaction completion. The agitation was reduced to 100 RPM and the batch was held overnight at 40° C.

The batch was cooled to 35° C., agitation was increased to 150 RPM, and 7.2 kg of 40% aqueous potassium carbonate was charged to the reactor. To the reactor was charged a solution of 158 g sodium metabisulfite in 4 L of purified water followed by a rinse of 2.2 kg of purified water. The batch was allowed to mix for 15 minutes at 200 RPM. The batch was cooled to 30° C. To the reactor was charged 4.4 kg of 5-bromovalerylchloride over 20 minutes, keeping the temperature between 30 and 38° C. The addition line was flushed with 3.0 kg of THF. The batch was cooled to 25° C. and allowed to react for two hours. The batch was sampled after the two hour reaction time for reaction completion. To the batch was added an additional 0.3 kg of 5-bromovalerylchloride. The batch was allowed to react for one hour, and then the batch was sampled for reaction completion. The batch was filtered through a bag filter with a 5 micron polypropylene bag followed by two cartridge filters (0.5 micron followed by 0.2 micron). The filtration lasted 20 minutes. The reactor was rinsed with 14.2 kg of THF, and the rinse was discharged to the filtration train to wash the catalyst cake. The filtrate was collected in a fluorinated polypropylene drum.

The product solution was transferred to a 50 gallon glass-lined reactor. The batch was distilled under vacuum (pressure=100 mmHg; maximum jacket temp=50° C.) to an approximate volume of 38 L. To the batch was added 33.0 kg of 200 proof ethanol from a pressure cylinder over approximately 30 minutes. To the batch was charged 32 L of purified water over 30 minutes, keeping the temperature at 45-50° C. The batch was cooled to 20° C. over 90 minutes and allowed to mix at 20° C. for one hour. The batch was then discharged to a portable centrifuge dressed with a polypropylene bag. The solid product was isolated in approximately 15 minutes (86.9 kg centrate was collected). To the reactor was charged 30.0 kg of 200 proof ethanol. The solvent was discharged to the centrifuge to wash the cake. The cake wash and spin out lasted 25 minutes; 32.8 kg centrate was collected. The wet cake (9.3 kg) was dried at 65° C. under vacuum for 28.5 hours to give 9.3 kg of the desired amide.

Example 5

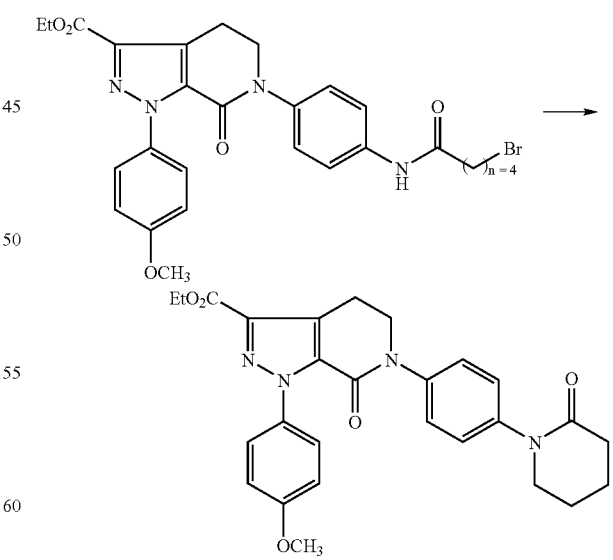

To a 50 gallon glass lined reactor was added 16.7 kg of the product from Example 4. The reactor was inerted and 74.0 kg of tetrahydrofuran were charged to the reactor. To the reactor was added 11.7 kg of potassium ethoxide (24% solution in ethanol) by deadhead vacuum over nine minutes. The batch temperature was allowed to rise, but not exceed 40° C. The transfer line was immediately rinsed with one liter of THF. When the batch reached 40° C., 180 g of glacial acetic acid were charged by deadhead vacuum to the reactor. The transfer line was rinsed with one liter of purified water. To the reactor were charged 50 g of PicaChem 80PN activated carbon and 16 liters of purified water. The batch was mixed for 30 minutes and sampled to check pH (about 7.3). The batch was filtered through a bag filter with a 1.0 micron polypropylene bag followed by two polypropylene cartridge filters 0.5 micron then 0.2 micron) and transferred into a 100 gallon glass-lined reactor, with the jacket temperature at 45° C. To the 50 gallon reactor was charged 7.0 kg of tetrahydrofuran. The THF was transferred through the filter train and into the 100 gallon reactor.

To the 100 gallon reactor was then charged 130 liters of purified water. The reactor contents were held at 45±3° C. for one hour. The batch was cooled to 5±3° C. over two hours, and held at 5±3° C. with mixing for one hour. The solid product was isolated on a portable centrifuge dressed with a 1-3 micron polypropylene bag. The isolation lasted one hour (214.9 kg centrate collected). To the 100 gallon reactor was charged 100 liters of purified water, and this water was discharged from the reactor to the centrifuge to wash the cake. The cake wash time was 30 minutes, and 103.5 kg centrate was collected. To the 100 gallon reactor was charged 29.0 kg of ethyl acetate which was cooled to 5±3° C. The solvent was discharged from the reactor to the centrifuge. The cake wash time was 30 minutes, and 36.6 kg of centrate was collected. The cake was dried at 70° C. under vacuum for 24.5 hours to give 10.7 kg of dried the desired lactam.

Example 6

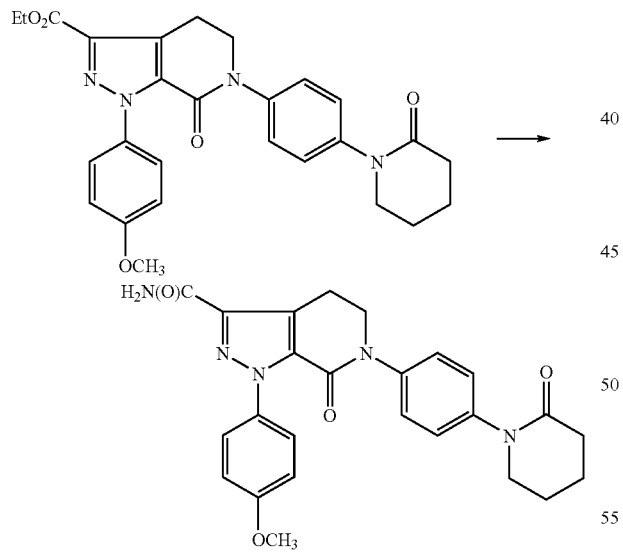

To a 100 gal glass-lined reactor was charged 73.0 kg propylene glycol USP followed by 10.0 kg of the product from Example 5. The reactor was inserted with nitrogen and heated to 35° C. Anhydrous ammonia (6.8 kg, 99.99%) was fed from a compressed gas cylinder using hot water to effect vaporization. A total of 6.8 kg ammonia (20 eq) was added over four hours while maintaining 35° C. batch temperature. The reactor pressure was 930 to 940 torr and the jacket temperature was 26.6° C. throughout most of the addition. After the addition was complete, the batch was heated to 90° C. over two hours. No foaming was observed. The batch was allowed to mix for 12 hours at 150 RPM and 90° C. The pressure was kept at approximately 45 psig.

The batch was cooled to 40° C. over 2.5 hours and agitation was slowed to 75 RPM to minimize crystal attrition. The ammonia was vented to the scrubber. The reactor was pressurized to 1200 mmHg with nitrogen and then vented to the acetic acid scrubber. The batch was sampled for reaction completion and for crystal form. The batch was heated to 90° C. and mixed at 150 RPM for four hours. The batch was cooled to 40° C. over two hours and sampled for crystal form. The batch was held overnight with agitation at 50 RPM.

The batch was then heated to 115° C. and mixed at 150 RPM. When the batch temperature stabilized, 30 g of form N-1 seeds in 1.1 kg propylene glycol USP were charged. After the seeds were added, the batch was allowed to mix at 115° C. for three hours. The batch was cooled to for sampling. The batch was heated back to 115° C. and mixed for 30 minutes. The batch was then cooled to 90° C. over seventy minutes. The headspace reverted to the vapor mist, but the batch was seeded anyway at 90.9° C. with 25.6 g seeds in 0.8 kg propylene glycol USP. The batch was held at 89-91° C. for 15 minutes, and then cooled to 50° C. over two hours. The batch was sampled for crystal form.

To the reactor was added 83 kg purified water over 28 minutes, keeping the batch temperature above 40° C., and the batch was mixed at 100 RPM for 30 minutes. The batch was cooled to 20° C. over 90 minutes and mixed at 20° C. for 30 minutes. The solid product was isolated on a centrifuge (fitted with polypropylene bag). To the reactor was charged 60 kg of purified water; the water was discharged to the centrifuge to wash the cake. This procedure was repeated twice for a total of 180 kg purified water wash. The wet cake (9.1 kg) was dried at 65° C. under vacuum for 31 hours to give 8.9 kg of the desired amide.

Example 7

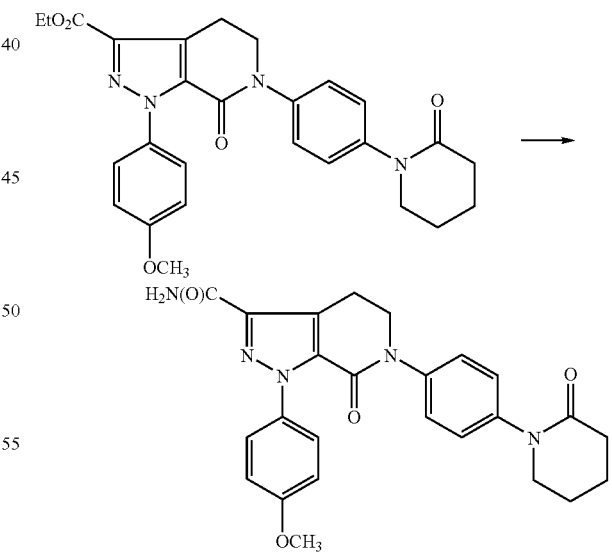

The ethyl ester (10 g) was dissolved in N,N-dimethylformamide (60 mL) and formamide (20 mL) at 50° C. The water content of the solution was determined by the Karl Fisher (KF) method (0.18 wt %). Trimethyl orthoformate (1.2 mL) and trifluoroacetic acid (0.3 mL) were added, and the mixture was agitated for 30 min at 50° C. Repeated KF analysis detected 0.01 wt % water. Sodium methoxide solution in methanol (6.1 mL, 25 wt %) was added, and the mixture was agitated for 2 h, at which point the reaction was complete by HPLC. Water (60 mL) was added at 50° C., and the resulting slurry was cooled to 25° C. and agitated for 2 h. The product was filtered and washed with water (2×100 mL) and tert-butyl methyl ether (50 mL). After drying in a vacuum oven at 70° C., 8.2 g (87% yield) of an off white amide were isolated (polymorph form H2-2).

Example 8

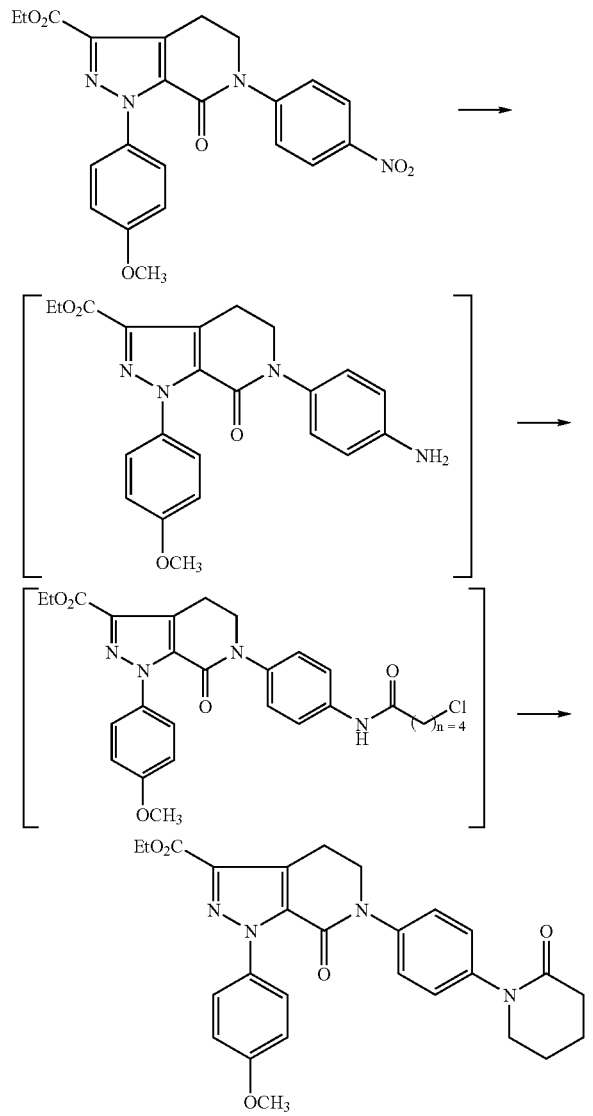

In a 100 mL Autoclave, inerted by $N_2$, were added the nitro-compound from Example 3 (8.75 g), 5% Pd/$Al_2O_3$ (0.88 g) type C5941 (Johnson Matthey), and NMP (50 mL). The reactor was pressurized with 25 psig of hydrogen for 3 h at 25° C. After depressurization, the suspension was filtered on buchner funnel. The cake was washed three times with NMP (8 mL). The aniline was obtained in 96% yield as a solution in NMP.

A solution of the aniline (17.88 g) in NMP (175 mL) was treated with of chlorovaleryl chloride (CVC)(8.00 mL) maintaining the internal temperature between 20 and 36° C. After 1 h, the reaction was complete.

Triethylorthoformate (38.10 mL) and TFA (0.70 mL) were added to the CVC addition product. After 1 h, a KF measurement showed water level at 234 ppm. NaOEt (60.2 mL, 21 w % in EtOH) was added dropwise. The internal temperature was maintained between 20 and 30° C. The cyclization was achieved in 3 h. TFA (6.80 mL) was added dropwise. After 0.5 h, water (175 mL) was added over 0.5 h. After 3 h, the solid was filtered and rinse twice with water (175 mL) and twice with MTBE (175 mL), and dried for 12 h in a vacuum oven (60° C., 25 mmHg). The lactam was obtained in 79% yield (17.00 g).

Example 9

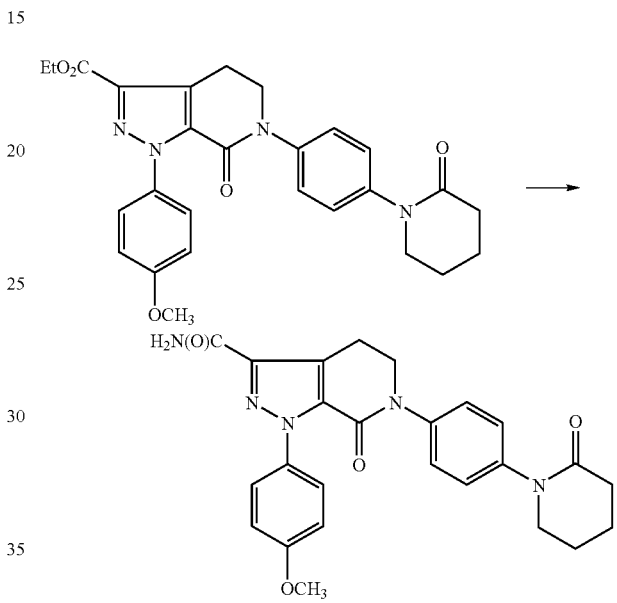

The ethyl ester (1 kg) was charged into a reactor along with anhydrous N,N-dimethylformamide (7.55 kg) and formamide (2.26 kg, 99.5+%, Aldrich). The mixture was agitated and warmed to 48-52° C. The water content of the solution was determined by the Karl Fisher (KF) method (0.18 wt %). Trimethyl orthoformate (0.1376 kg) and trifluoroacetic acid (0.047 kg) were added, and the mixture was agitated for 30 min at 48-52° C. Repeated KF analysis detected 0.03 wt % water. Sodium methoxide solution in methanol (0.7866 kg) was added, and the mixture was agitated for 30 min, at which point the reaction was complete by HPLC. Water (0.4 kg) was added at 48-52° C., and the solution was agitated and cooled to 20-25° C. for 2 h. Water (7.6 kg) was added at 17-20° C. within 1 h. The resulting slurry was agitated at 17-20° C. for about 1-2 h. The slurry was sampled for completion of crystallization.

The slurry (1 L) was transferred to a transient tank, heated to 55-60° C., and sheared and agitated to transform the polymorph from H2-2 to small granular N-1 crystals. After completion of polymorph transformation as shown by Raman and Lasentec, the remaining slurry was transferred to the transient tank while maintaining a tank temperature of 55-60° C. The slurry was sheared and agitated to form the small granular N-1 crystals. The slurry was continuously decanted to a receiver tank (kept at 55° C.), while maintaining a liquid lever of 1 L. The receiver tank was cooled to 20° C. over 2-3 hours. The slurry was filtered, washed with water (3×5 kg) and isopropanol (1×4 kg), and dried in a vacuum oven at 50° C. to yield the final product as N-1 crystals (0.80-0.85 kg, 85-90% yield).

Xray Diffraction: Characteristic diffraction peak positions (degrees 2θ±0.1)@RT, based on a high quality pattern collected with a diffractometer (CuKα) with a spinning capillary with 2θ calibrated with a NIST other suitable standard are shown in Table 1 below.

TABLE 1

| Form N-1 | Form H2-2 |
|---|---|
| 10.0 | 5.8 |
| 10.6 | 7.4 |
| 12.3 | 16.0 |
| 12.9 | 20.2 |
| 18.5 | 23.5 |
| 27.1 | 25.2 |

The SSNRM[13] shifts (δ) relative to tetramethyl silane (TMS) are: 20.5, 21.5, 24.5, 31.4, 51.7, 54.4, 113.4, 117.1, 121.7, 125.4, 128.2, 128.9, 130.6, 131.7, 134.3, 141.8, 158.1, 160.0, 161.7, and 172.2 (ppm).

Data were collected on a Bruker-Nonius CAD4 serial diffractometer. (BRUKER AXS, Inc., 5465 East Cheryl Parkway Madison, Wis. 53711.) Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package in the Collect program suite. (See Otwinowski, Z. & Minor, W. (1997) in *Macromolecular Crystallography*, eds. Carter, W. C. Jr & Sweet, R. M. (Academic, NY), Vol. 276, pp. 307-326 and Collect Data collection and processing user interface: Collect: Data collection software, R. Hooft, Nonius B. V., 1998) When indicated, crystals were cooled in the cold stream of an Oxford cryo system during data collection. (See Oxford Cryosystems Cryostream cooler: J. Cosier and A. M. Glazer, J. Appl. Cryst., 1986, 19, 105.) The structures were solved by direct methods and refined on the basis of observed reflections using either the SDP software package (Structure Determination Package, Enraf-Nonius, Bohemia NY 11716.) with minor local modifications or the crystallographic package, MAXUS. (maXus solution and refinement software suite: S. Mackay, C. J. Gilmore, C. Edwards, M. Tremayne, N. Stewart, K. Shankland.)

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R^w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

Crystallographic Data: The Unit Cell Data for Form N-1 and Form H2-2 and the Positional Parameters for Form N-1 and Form H2-2 are provided below in Tables 2-4.

TABLE 2

Unit cell Data for Form N-1 and Form H2-2

| | Form | |
|---|---|---|
| | N-1 | H2-2 |
| Solvate | None | Dihydrate |
| T | +22 | +22 |
| a(Å) | 10.233(1) | 6.193(1) |
| b(Å) | 13.852(1) | 30.523(1) |
| c(Å) | 15.806(1) | 13.046(1) |
| α, ° | 90 | 90 |
| β, ° | 92.98(1) | 90.95(1) |
| γ, ° | 90 | 90 |
| V(Å³) | 2237.4(5) | 2466.0(5) |
| Z' | 1 | 1 |
| Vm | 559 | 617 |
| SG | P2$_1$/n | P2$_1$/n |
| Dcalc | 1.364 | 1.335 |
| R | 0.05 | 0.09 |
| Sol. sites | None | 2 H$_2$O |

Z' is the number of molecules per asymmetric unit.
T(° C.) is the temperature for the crystallographic data.
Vm = V(unit cell)/(ZZ')

TABLE 3

Table of Positional Parameters and Their Estimated Standard Deviations for Form N-1 at rt

| Atom | x | y | z | B(iso) |
|---|---|---|---|---|
| O8 | 0.1360(2) | 0.1966(1) | 0.01579(8) | 3.0 |
| O16 | 0.0088(2) | 0.1334(1) | 0.40902(9) | 3.8 |
| O26 | 0.5315(1) | −0.1861(1) | −0.11407(9) | 3.3 |
| O31 | 0.2156(2) | 0.6096(1) | −0.0274(1) | 4.2 |
| N1 | 0.1306(2) | 0.2981(1) | 0.18364(9) | 2.3 |
| N2 | 0.1013(2) | 0.3134(1) | 0.2651(1) | 2.5 |
| N7 | 0.1754(2) | 0.0576(1) | 0.0905(1) | 2.4 |
| N17 | 0.0573(2) | 0.2910(1) | 0.4359(1) | 3.5 |
| N24 | 0.3408(2) | −0.1573(1) | −0.1877(1) | 2.5 |
| C3 | 0.0885(2) | 0.2251(2) | 0.2983(1) | 2.3 |
| C4 | 0.1113(2) | 0.1528(1) | 0.2389(1) | 2.2 |
| C5 | 0.1112(2) | 0.0450(2) | 0.2398(1) | 2.8 |
| C6 | 0.2041(2) | 0.0114(2) | 0.1740(1) | 3.1 |
| C8 | 0.1520(2) | 0.1551(1) | 0.0835(1) | 2.2 |
| C9 | 0.1380(2) | 0.2016(1) | 0.1667(1) | 2.1 |
| C10 | 0.1564(2) | 0.3793(1) | 0.1307(1) | 2.3 |
| C11 | 0.2603(2) | 0.3755(1) | 0.0785(1) | 2.5 |
| C12 | 0.2840(2) | 0.4519(2) | 0.0251(1) | 2.7 |
| C13 | 0.2036(2) | 0.5322(2) | 0.0246(1) | 3.0 |
| C14 | 0.1018(2) | 0.5367(2) | 0.0799(2) | 3.4 |
| C15 | 0.0771(2) | 0.4602(2) | 0.1320(1) | 3.0 |
| C16 | 0.0487(2) | 0.2119(2) | 0.3863(1) | 2.6 |
| C18 | 0.2125(2) | 0.0054(1) | 0.0172(1) | 2.3 |
| C19 | 0.3135(2) | 0.0384(2) | −0.0296(1) | 3.3 |
| C20 | 0.3538(2) | −0.0144(2) | −0.0974(1) | 3.3 |
| C21 | 0.2945(2) | −0.1014(2) | −0.1186(1) | 2.4 |
| C22 | 0.1918(2) | −0.1337(2) | −0.0730(1) | 2.8 |
| C23 | 0.1494(2) | −0.0796(2) | −0.0058(1) | 2.7 |
| C25 | 0.4613(2) | −0.1971(2) | −0.1791(1) | 2.5 |
| C27 | 0.5100(2) | −0.2545(2) | −0.2518(1) | 4.0 |
| C28 | 0.4054(3) | −0.2916(2) | −0.3143(2) | 5.4 |
| C29 | 0.3065(3) | −0.2153(2) | −0.3352(2) | 5.6 |
| C30 | 0.2458(3) | −0.1766(2) | −0.2592(1) | 4.0 |
| C32 | 0.3098(3) | 0.6021(2) | −0.0898(2) | 4.8 |
| H171 | 0.094 | 0.358 | 0.411 | 4.5 |
| H172 | 0.029 | 0.287 | 0.501 | 4.5 |

Occupancies are 1 unless otherwise noted

TABLE 4

Table of Positional Parameters and Their Estimated Standard Deviations for Form H2-2 at rt

| Name | x | y | z | Occupancy | B(iso) |
|---|---|---|---|---|---|
| O8 | 0.7032(6) | 0.3398(10) | −0.1082(3) | 1.00 | 5.0 |
| O16 | 0.2493(8) | 0.1447(13) | −0.1442(4) | 1.00 | 7.6 |
| O25 | −0.0325(7) | 0.4645(14) | 0.2292(4) | 1.00 | 7.1 |
| O13 | 1.3402(7) | 0.3278(18) | −0.4608(4) | 1.00 | 8.4 |
| O98 | 0.1958(10) | −0.0223(5) | 0.0182(14) | 0.50 | 14.3 |
| O99 | 0.2663(10) | 0.0560(2) | −0.0685(9) | 0.65 | 15.7 |
| N1 | 0.6878(7) | 0.2560(16) | −0.2286(3) | 1.00 | 3.8 |
| N2 | 0.6472(7) | 0.2136(16) | −0.2488(3) | 1.00 | 4.4 |
| N7 | 0.3698(7) | 0.3213(13) | −0.0453(3) | 1.00 | 3.4 |
| N17 | 0.5102(8) | 0.1300(15) | −0.2567(4) | 1.00 | 7.2 |
| N24 | 0.2839(7) | 0.4834(13) | 0.1581(3) | 1.00 | 4.2 |
| C3 | 0.4802(9) | 0.2021(17) | −0.1907(4) | 1.00 | 3.9 |
| C4 | 0.4094(8) | 0.2375(17) | −0.1318(4) | 1.00 | 3.6 |
| C5 | 0.2323(8) | 0.2442(16) | −0.0581(4) | 1.00 | 4.0 |
| C6 | 0.1732(8) | 0.2933(16) | −0.0546(4) | 1.00 | 3.7 |
| C8 | 0.5491(10) | 0.3142(19) | −0.1031(4) | 1.00 | 3.8 |
| C10 | 0.8495(9) | 0.2774(2) | −0.2855(4) | 1.00 | 3.6 |
| C9 | 0.5443(8) | 0.2715(17) | −0.1570(4) | 1.00 | 3.8 |
| C15 | 1.0313(8) | 0.2514(19) | −0.3108(5) | 1.00 | 5.0 |
| C14 | 1.1912(10) | 0.2708(2) | −0.3707(5) | 1.00 | 6.0 |
| C13 | 1.1742(10) | 0.3130(3) | −0.4000(5) | 1.00 | 5.8 |
| C12 | 0.9882(11) | 0.3388(19) | −0.3792(5) | 1.00 | 5.4 |
| C11 | 0.8278(9) | 0.3187(3) | −0.3204(4) | 1.00 | 4.8 |
| C16 | 0.4013(11) | 0.1564(19) | −0.1941(4) | 1.00 | 4.9 |
| C18 | 0.3490(9) | 0.3621(17) | 0.0050(4) | 1.00 | 3.9 |
| C19 | 0.5074(8) | 0.3764(18) | 0.0768(4) | 1.00 | 4.6 |
| C20 | 0.4881(9) | 0.4158(19) | 0.1269(4) | 1.00 | 4.4 |
| C21 | 0.3016(9) | 0.4418(17) | 0.1067(4) | 1.00 | 4.2 |
| C22 | 0.1457(8) | 0.4288(17) | 0.0363(4) | 1.00 | 4.3 |
| C23 | 0.1698(9) | 0.3883(18) | −0.0139(4) | 1.00 | 3.8 |
| C25 | 0.1187(10) | 0.4913(19) | 0.2178(5) | 1.00 | 5.1 |
| C26 | 0.1017(11) | 0.5351(2) | 0.2753(6) | 1.00 | 7.7 |
| C27 | 0.2873(14) | 0.5621(3) | 0.2723(8) | 1.00 | 11.2 |
| C28 | 0.4518(14) | 0.5535(2) | 0.2061(10) | 1.00 | 13.1 |
| C29 | 0.4672(10) | 0.5134(2) | 0.1515(5) | 1.00 | 7.3 |
| C30 | 1.3332(12) | 0.3720(3) | −0.4906(6) | 1.00 | 9.5 |
| H171 | 0.6494 | 0.1414 | −0.2982 | 1.00 | 8.2 |
| H172 | 0.4571 | 0.0962 | −0.2676 | 1.00 | 8.2 |

Numerous modifications and variations of the present invention are possible in light of the above teachings. It is therefore to be understood that within the scope of the appended claims, the invention may be practiced otherwise than as specifically described herein.

What is claimed is:

1. A process for preparing a compound of formula III, comprising:
    (a) contacting a compound of formula I with a compound of formula II in the presence of a first base;

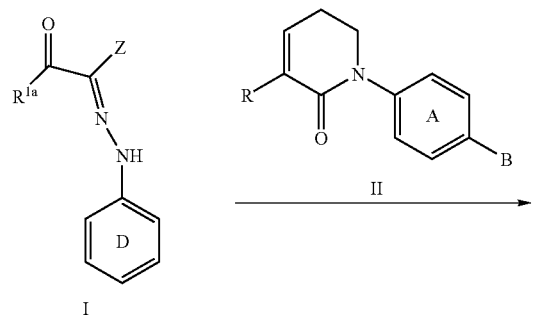

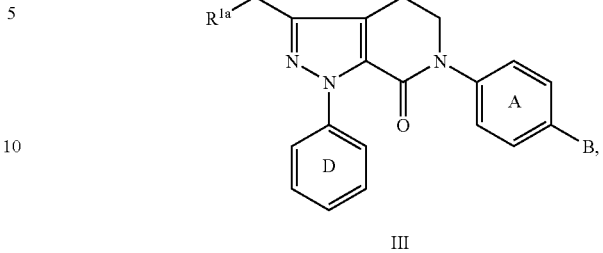

wherein:
  Z is selected from Cl, Br, I, OSO$_2$Me, OSO$_2$Ph, and OSO$_2$Ph-p-Me;
  ring D is selected from phenyl, 2-fluorophenyl, 3-chlorophenyl, and 4-methoxyphenyl;
  $R^{1a}$ is selected from CH$_3$, CH$_2$CH$_3$, CH$_2$CH$_2$CH$_3$, OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, OC(CH$_3$)$_3$, O-phenyl, OCH$_2$-phenyl, OCH$_2$CH$_2$-phenyl, and OCH$_2$CH$_2$H$_2$-phenyl;
  R is selected from Cl, Br, and I;
  ring A is substituted with 0-1 R$^4$;
  B is NO$_2$; and
  R$^4$ is selected from H, OH, OCH$_3$, OCH$_2$CH$_3$, OCH$_2$CH$_2$CH$_3$, OCH(CH$_3$)$_2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, and CF$_3$.

2. A process according to claim 1, wherein:
  Z is selected from Cl, Br, and I;
  ring D is selected from 3-chlorophenyl and 4-methoxyphenyl;
  $R^{1a}$ is selected from OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, and OC(CH$_3$)$_3$;
  ring A is substituted with 0-1 R$^4$; and
  R$^4$ is selected from H and F.

3. A process according to claim 2, wherein:
  Z is Cl;
  ring D is 4-methoxyphenyl;
  $R^{1a}$ is OCH$_2$CH$_3$;
  R is Cl; and
  ring A is unsubstituted.

4. A process according to claim 1, wherein: in reaction (a), the compound of formula I is contacted with the compound of formula II followed by the addition of the first base.

5. A process according to claim 4, wherein: the first base in reaction (a) is a substituted amine base.

6. A process according to claim 5, wherein: the substituted amine base is selected from: triethylamine, diisopropylethylamine, dabco, DBN, DBU, and N-methylmorpholine.

7. A process according to claim 6, wherein: the substituted amine base is triethylamine.

8. A process according to claim 1, wherein: in reaction (a), the contacting is performed in the presence of a first aprotic solvent.

9. A process according to claim 8, wherein: the first aprotic solvent is toluene.

10. A process according to claim 1, wherein: reaction (a) further comprises contacting with a first strong acid.

11. A process according to claim 10, wherein: the first acid is HCl.

12. A process for preparing a compound of formula IV:

III ⟶

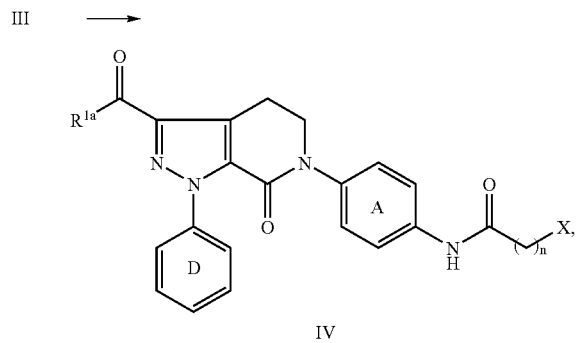

IV the process comprising:
(b) reducing the B group of formula III to an amino group in the presence of hydrogen and Pd/Al$_2$O$_3$, and a second aprotic solvent; and
(c) contacting the resulting amino compound with an alkyl-acid halide to form a compound of formula IV, wherein:
the alkyl-acid halide is X-C$_{3-5}$-alkylene-C(O)-X$_1$;
X is selected from Cl, Br, and I;
X$_1$ is selected from the group Cl, Br, OS(O)$_2$CH$_3$, OS(O)$_2$CF$_3$, OS(O)$_2$-phenyl, and OS(O)$_2$-tolulyl;
n is selected from the group 3, 4, and 5;
ring D is selected from phenyl, 2-fluorophenyl, 3-chlorophenyl, and 4-methoxyphenyl;
R$^{1a}$ is selected from CH$_3$, CH$_2$CH$_3$, CH$_2$CH$_2$CH$_3$, OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, OC(CH$_3$)$_3$, O-phenyl, OCH$_2$-phenyl, OCH$_2$CH$_2$-phenyl, and OCH$_2$CH$_2$CH$_2$-phenyl;
ring A is substituted with 0-1 R$^4$;
B is NO$_2$; and
R$^4$ is selected from H, OH, OCH$_3$, OCH$_2$CH$_3$, OCH$_2$CH$_2$CH$_3$, OCH(CH$_3$)$_2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, and CF$_3$.

13. A process according to claim 12, wherein:
the alkyl-acid halide is X-(CH$_2$)$_4$-C(O)-X$_1$;
X is selected Cl and Br;
X$_1$ is Cl;
n is 4;
ring D is selected from 3-chlorophenyl and 4-methoxyphenyl;
R$^{1a}$ is selected from OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, and OC(CH$_3$)$_3$;
ring A is substituted with 0-1 R$^4$; and
R$^4$ is selected from H and F.

14. A process according to claim 13, wherein:
X is Cl;
X$_1$ is Cl;
n is 4;
ring D is 4-methoxyphenyl;
R$^{1a}$ is OCH$_2$CH$_3$; and
ring A is unsubstituted.

15. A process according to claim 14, wherein in reaction (b), the second aprotic solvent is selected from N-methylpyrrolidinone, DMSO, DMF, and DMAC.

16. A process according to claim 15, wherein in reaction (b), the second aprotic solvent is N-methylpyrrolidinone.

17. A process according to claim 12, wherein a reduction solution resulting from reaction (b) is filtered prior to contacting with the alkyl-acid halide in reaction (c).

18. A process for preparing a compound of formula V:

IV ⟶

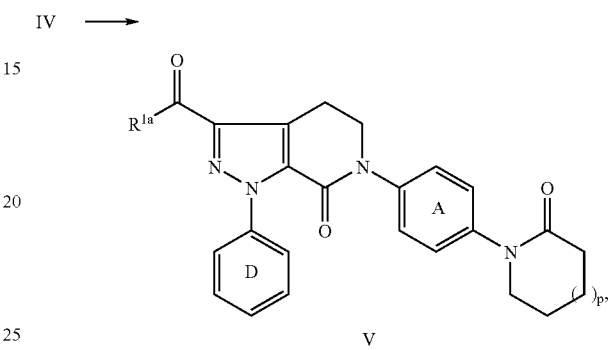

V the process comprising:
(d) cyclizing the compound of formula IV to form a compound of formula V, wherein:
p is selected from 0, 1, and 2;
ring D is selected from phenyl, 2-fluorophenyl, 3-chlorophenyl, and 4-methoxyphenyl;
R$^{1a}$ is selected from CH$_3$, CH$_2$CH$_3$, CH$_2$CH$_2$CH$_3$, OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, OC(CH$_3$)$_3$, O-phenyl, OCH$_2$-phenyl, OCH$_2$CH$_2$-phenyl, and OCH$_2$CH$_2$CH$_2$-phenyl;
ring A is substituted with 0-1 R$^4$; and
R$^4$ is selected from H, OH, OCH$_3$, OCH$_2$CH$_3$, OCH$_2$CH$_2$CH$_3$, OCH(CH$_3$)$_2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, CH(CH$_3$)$_3$, —CN, and CF$_3$.

19. A process according to claim 18, wherein:
p is 1;
ring D is selected from 3-chlorophenyl and 4-methoxyphenyl;
R$^{1a}$ is selected from OCH$_3$, OCH$_2$CH$_3$, OCH$_2$CH$_2$CH$_3$, OCH(CH$_3$)$_2$, OCH$_2$CH$_2$CH$_2$CH$_3$, OCH(CH$_3$)CH$_2$CH$_3$, OCH$_2$CH(CH$_3$)$_2$, and OC(CH$_3$)$_3$;
ring A is substituted with 0-1 R$^4$; and
R$^4$ is selected from H and F.

20. A process according to claim 19, wherein:
p is 1;
ring D is 4-methoxyphenyl;
R$^{1a}$ is OCH$_2$CH$_3$; and
ring A is unsubstituted.

21. A process according to claim 18, wherein reaction (d) is performed in the presence of first chemical dehydrating agents.

22. A process according to claim 21, wherein the first chemical dehydrating agents are a second strong acid and a first orthoformate.

23. A process according to claim 22, wherein the second strong acid is TFA and the first orthoformate is triethyl orthoformate.

24. A process according to claim 21, wherein a sodium alkoxide is added after compound IV has been contacted with the first chemical dehydrating agents.

25. A process according to claim 24, wherein the sodium alkoxide is sodium ethoxide.

26. A process according to claim 18, wherein cyclizing reaction (d) is performed in the presence of a third aprotic solvent.

27. A process according to claim 26, wherein the third aprotic solvent is N-methylpyrrolidinone.

28. A process for preparing a compound of formula VI:

IV ⟶

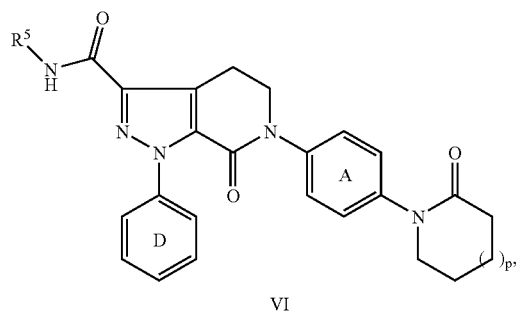

VI the process comprising:
(e) amidating ester $R^{1a}$ of the compound of formula V to form a compound of formula VI,
wherein:
p is selected from 0, 1, and 2;
ring D is selected from phenyl, 2-fluorophenyl, 3-chlorophenyl, and 4-methoxyphenyl;
$R^{1a}$ is selected from $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
ring A is substituted with 0-1 $R^4$;
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$; and
$R^5$ is selected from H, $CH_3$, and $CH_2CH_3$;
wherein in reaction (e), the compound of formula V and a fourth aprotic solvent are contacted with second chemical dehydrating agents prior to contacting with a second base.

29. A process according to claim 28, wherein:
p is 1;
ring D is selected from 3-chlorophenyl and 4-methoxyphenyl;
$R^{1a}$ is $CO_2CH_2CH_3$;
ring A is substituted with 0-1 $R^4$;
$R^4$ is selected from H and F; and
$R^5$ is H.

30. A process according to claim 29, wherein:
p is 1;
ring D is 4-methoxyphenyl;
$R^{1a}$ is $CO_2CH_2CH_3$; and
ring A is unsubstituted.

31. A process according to claim 29, wherein reaction (e) is performed by contacting the compound of formula V with a formamide in the presence of the second base and the fourth aprotic solvent, wherein:
the formamide is $HC(O)NHR^5$;
the second base is an alkoxide; and
$R^5$ is selected from H, $CH_3$, and $CH_2CH_3$.

32. A process according to claim 31, wherein:
the formamide is $HC(O)NH_2$;
the second base is a $C_{1-6}$ alkoxide and a counterion is selected from Li, Na, K, Li, and Mg; and
the fourth aprotic solvent is DMF.

33. A process according to claim 28, wherein, in reaction (e), the second chemical dehydrating agents are selected from the group consisting of trimethyl orthoformate, triethyl orthoformate, diethyl phenyl orthoformate, tributyl orthoformate, triisopropyl orthoformate, tripentyl orthoformate, tripropyl orthoformate, trifluoroacetic acid, sulfuric acid, and sulfonic acid.

34. A process for preparing a compound of formula V:

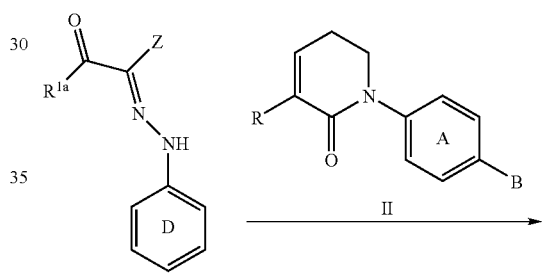

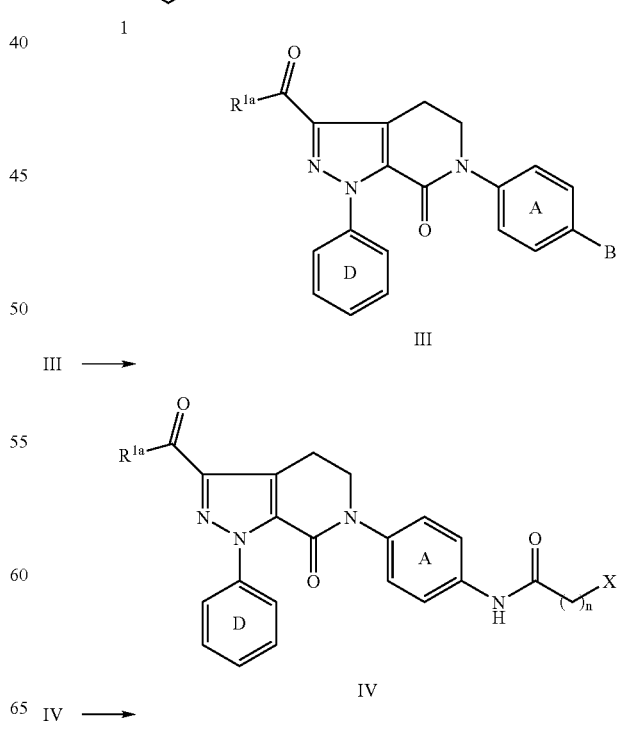

IV ⟶

-continued

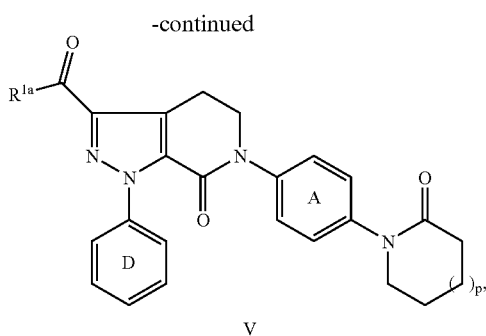

the process comprising:
contacting a compound of formula I with a compound of formula II in the presence of a first base;
reducing the B group of formula III to an amino group;
contacting the resulting amino compound with an alkyl-acid halide to form a compound of formula IV; and
cyclizing the compound of formula IV to form a compound of formula V,
wherein:
Z is selected from Cl, Br, I, $OSO_2Me$, $OSO_2Ph$, and $OSO_2Ph\text{-}p\text{-}Me$; alkyl-acid halide is $X\text{-}C_{3\text{-}5}\text{-alkylene-}C(O)\text{-}X_1$;
X is selected from Cl, Br, and I;
$X_1$ is selected from Cl, Br, $OS(O)_2CH_3$, $OS(O)_2CF_3$, $OS(O)_2$-phenyl, and $OS(O)_2$-tolulyl;
n is selected from 3, 4, and 5;
p is selected from 0, 1, and 2;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, $OC(CH_3)_3$, O-phenyl, $OCH_2$-phenyl, $OCH_2CH_2$-phenyl, and $OCH_2CH_2CH_2$-phenyl;
R is selected from Cl, Br, and I;
ring A is substituted with 0-1 $R^4$;
B is $NO_2$; and
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$.

35. A process according to claim 34, wherein:
Z is selected from Cl, Br, or I;
the alkyl-acid halide is $X\text{-}(CH_2)_4\text{-}C(O)\text{-}X_1$;
X is selected Cl and Br;
$X_1$ is Cl;
n is 4;
p is 1;
ring D is selected from 3-chlorophenyl, and 4-methoxyphenyl;
$R^{1a}$ is selected from $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;
R is selected from Cl, Br, and I;
ring A is substituted with 0-1 $R^4$;
B is $NO_2$; and
$R^4$ is selected from H and F.

36. A process according to claim 35, wherein:
Z is Cl;
alkyl-acid halide is $Cl\text{-}(CH_2)_4\text{-}C(O)\text{-}Cl$;
n is 4;
p is 1;
ring D is 4-methoxyphenyl;
$R^{1a}$ is $OCH_2CH_3$;
R is Cl;
ring A is unsubstituted; and
B is $NO_2$.

37. A process for preparing a compound of formula VI:

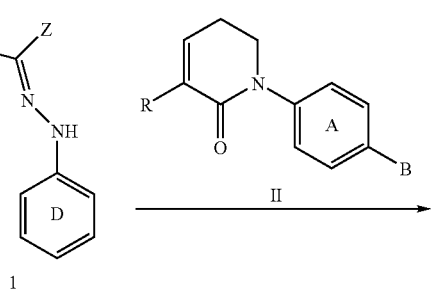

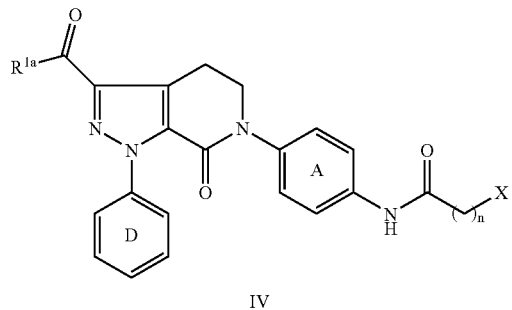

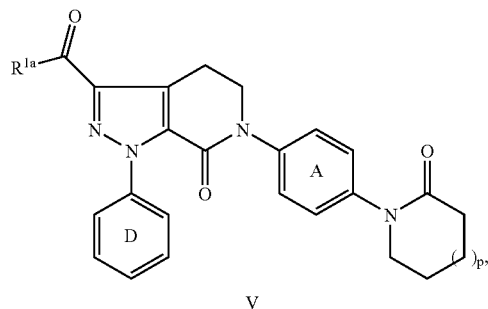

-continued

VI

[Structure VI: pyrazolopyridinone with R⁵NH-C(O)- substituent, D phenyl on N1, linked to phenyl ring A bearing N-piperidinone substituent]

the process comprising:
- contacting a compound of formula I with a compound of formula II in the presence of a first base;
- reducing the B group of formula III to an amino group;
- contacting the resulting amino compound with an alkyl-acid halide to form a compound of formula IV;
- cyclizing the compound of formula IV to form a compound of formula V; and
- amidating ester $R^{1a}$ of the compound of formula V to form a compound of formula VI, wherein:
Z is selected from Cl, Br, I, $OSO_2Me$, $OSO_2Ph$, and $OSO_2Ph$-p-Me; alkyl-acid halide is X-$C_{3-5}$-alkylene-C(O)-$X_1$;
X is selected from Cl, Br, and I;
$X_1$ is selected from Cl, Br, $OS(O)_2CH_3$, $OS(O)_2CF_3$, $OS(O)_2$-phenyl, and $OS(O)_2$-tolulyl;
n is selected from 3, 4, and 5;
p is selected from 0, 1, and 2;
ring D is selected from phenyl, 2-fluorophenyl, 3-chlorophenyl, and 4-methoxyphenyl;
$R^{1a}$ is selected from $CH_3$, $CH_2CH_3$, $CH_2CH_2CH_3$, $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, OC $(CH_3)_3$, O-phenyl, $OCH_2$-phenyl, $OCH_2CH_2$-phenyl, and $OCH_2CH_2CH_2$-phenyl;
R is selected from Cl, Br, and I;
ring A is substituted with 0-1 $R^4$;
B is $NO_2$;
$R^4$ is selected from H, OH, $OCH_3$, $OCH_2CH_3$, $OCH_2CH_2CH_3$, $OCH(CH_3)_2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $CH(CH_3)_3$, —CN, and $CF_3$; and
$R^5$ is selected from H, $CH_3$, and $CH_2CH_3$.

38. A process according to claim 37, wherein:
Z is selected from Cl, Br, and I;
the alkyl-acid halide is X-$(CH_2)_4$-C(O)-$X_1$;
X is selected from Cl and Br;
$X_1$ is Cl;
n is 4;
p is 1;
ring D is selected from 3-chlorophenyl, and 4-methoxyphenyl;
$R^{1a}$ is selected from $OCH_3$, $OCH_2CH_3$, $OCH_2CH_2CH_3$, $OCH(CH_3)_2$, $OCH_2CH_2CH_2CH_3$, $OCH(CH_3)CH_2CH_3$, $OCH_2CH(CH_3)_2$, and $OC(CH_3)_3$;
R is selected from Cl, Br, and I;
ring A is substituted with 0-1 $R^4$;
B is $NO_2$; and
$R^4$ is selected from H and F.

39. A process according to claim 38, wherein:
Z is Cl;
the alkyl-acid halide is Cl-$(CH_2)_4$-C(O)-Cl;
n is 4;
p is 1;
ring D is 4-methoxyphenyl;
$R^{1a}$ is $OCH_2CH_3$;
R is Cl;
ring A is unsubstituted;
B is $NO_2$; and
is H.

* * * * *

UNITED STATES PATENT AND TRADEMARK OFFICE
CERTIFICATE OF CORRECTION

PATENT NO.         : 7,396,932 B2
APPLICATION NO.    : 11/235510
DATED              : July 8, 2008
INVENTOR(S)        : Rafael Shapiro et al.

It is certified that error appears in the above-identified patent and that said Letters Patent is hereby corrected as shown below:

COLUMN 32:

Line 25, "OCH$_2$CH$_2$H$_2$-phenyl;" should read --OCH$_2$CH$_2$CH$_2$-phenyl;--; and
Line 57, "dabco" should read --DABCO--.

COLUMN 33:

Line 50, "selected" should read --selected from--.

COLUMN 35:

Line 20, "IV" should read --V--.

COLUMN 36:

Line 17, "Li," (second occurrence) should be deleted.

COLUMN 37:

Line 51, "selected" should read --selected from--.

COLUMN 38:

Lines 55-65, " 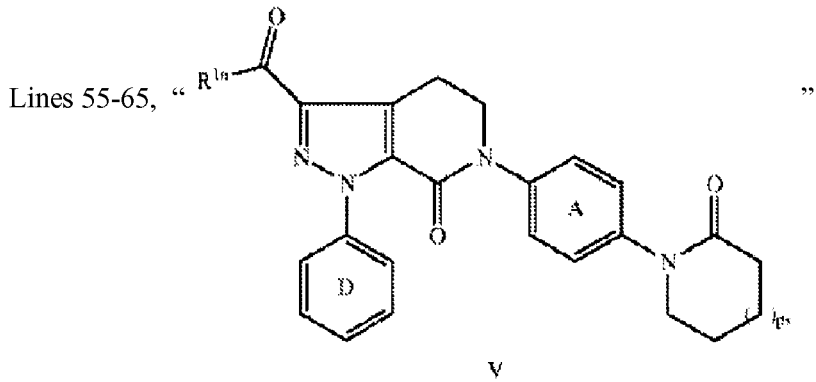 "

UNITED STATES PATENT AND TRADEMARK OFFICE
CERTIFICATE OF CORRECTION

PATENT NO. : 7,396,932 B2
APPLICATION NO. : 11/235510
DATED : July 8, 2008
INVENTOR(S) : Rafael Shapiro et al.

It is certified that error appears in the above-identified patent and that said Letters Patent is hereby corrected as shown below:

should read

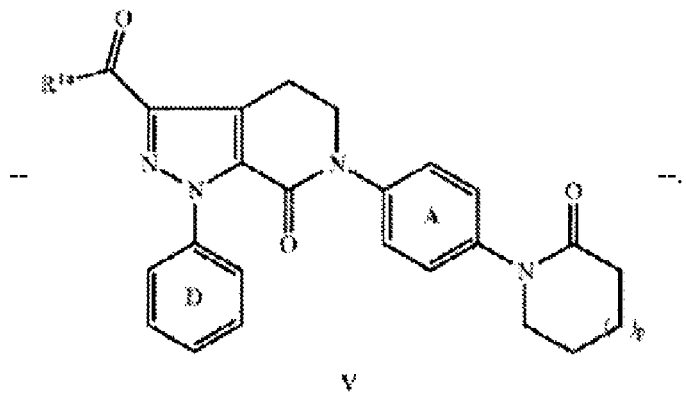

COLUMN 40:

Line 38, "is H." should read --$R^5$ is H.--.

Signed and Sealed this

Twelfth Day of May, 2009

JOHN DOLL
*Acting Director of the United States Patent and Trademark Office*